United States Patent
Wu et al.

(10) Patent No.: US 11,510,983 B2
(45) Date of Patent: Nov. 29, 2022

(54) METHOD AND APPARATUS FOR BOOSTING VACCINE EFFICACY

(71) Applicant: THE GENERAL HOSPITAL CORPORATION, Boston, MA (US)

(72) Inventors: Mei X. Wu, Lexington, MA (US); R. Rox Anderson, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 639 days.

(21) Appl. No.: 14/776,296

(22) PCT Filed: Mar. 13, 2014

(86) PCT No.: PCT/US2014/025659
§ 371 (c)(1),
(2) Date: Sep. 14, 2015

(87) PCT Pub. No.: WO2014/151403
PCT Pub. Date: Sep. 25, 2014

(65) Prior Publication Data
US 2016/0038591 A1    Feb. 11, 2016

Related U.S. Application Data

(60) Provisional application No. 61/789,775, filed on Mar. 15, 2013.

(51) Int. Cl.
*A61M 37/00* (2006.01)
*A61K 41/00* (2020.01)
(Continued)

(52) U.S. Cl.
CPC .......... *A61K 41/0052* (2013.01); *A61K 39/12* (2013.01); *A61K 39/145* (2013.01);
(Continued)

(58) Field of Classification Search
CPC .......... A61K 41/0052; A61M 37/0092; A61M 2037/0007; A61M 2018/143; A61B 2017/00765
See application file for complete search history.

(56) References Cited

U.S. PATENT DOCUMENTS

| | | | |
|---|---|---|---|
| 2001/0050083 A1* | 12/2001 | Marchitto | A61B 5/411 128/898 |
| 2005/0049582 A1* | 3/2005 | DeBenedictis | A61B 18/20 606/9 |

(Continued)

FOREIGN PATENT DOCUMENTS

WO    2013/033496    3/2013

OTHER PUBLICATIONS

Schwan, H.P., Ultrasound and Electromagnetic Radiation in Hyperthermia—A Historical Perspective, Br. J. Cancer Suppl., Mar. 1982, vol. 5, pp. 84-92, p. 85, col. 2, paragraph 3, p. 91, col. 1, paragraphs 2, 4.*

(Continued)

*Primary Examiner* — Nathan R Price
*Assistant Examiner* — Courtney B Fredrickson
(74) *Attorney, Agent, or Firm* — Quarles and Brady

(57) ABSTRACT

A method and an system for vaccinating a mammalian subject. The method includes the steps of: arranging a source of electromagnetic radiation proximate to a target zone of skin of the mammalian subject; controlling the source of electromagnetic radiation to deliver a dose of electromagnetic radiation to the target zone determined to create one or more thermally-denatured zones in the target zone; and intradermally injecting a vaccine within the target zone to vaccinate the mammalian subject. The system for vaccinating a subject may include an electromagnetic radiation source configured to be arranged proximate to a target zone on an exterior of the subject; a user control configured to (Continued)

selectively cause the electromagnetic radiation source to deliver a dose of electromagnetic radiation toward the target zone to create one or more thermally-denatured zones in the target zone; and a vaccine-delivery system configured to deliver a vaccine to the target zone.

17 Claims, 33 Drawing Sheets

(51) Int. Cl.
    *A61K 39/39*     (2006.01)
    *A61K 39/12*     (2006.01)
    *A61K 39/145*     (2006.01)
    *A61N 5/06*     (2006.01)
    *A61K 39/00*     (2006.01)
    *A61N 7/02*     (2006.01)
    *A61B 18/14*     (2006.01)

(52) U.S. Cl.
CPC .......... *A61K 39/39* (2013.01); *A61M 37/0092* (2013.01); *A61N 5/0625* (2013.01); *A61B 2018/143* (2013.01); *A61K 2039/54* (2013.01); *A61K 2039/55511* (2013.01); *A61K 2039/55588* (2013.01); *A61M 2037/0007* (2013.01); *A61M 2202/30* (2013.01); *A61N 7/02* (2013.01); *C12N 2760/16111* (2013.01); *C12N 2760/16134* (2013.01); *Y02A 50/30* (2018.01)

(56) References Cited

U.S. PATENT DOCUMENTS

| | | | | |
|---|---|---|---|---|
| 2005/0112135 | A1* | 5/2005 | Cormier | A61B 17/205 424/185.1 |
| 2006/0079947 | A1* | 4/2006 | Tankovich | A61N 5/062 607/89 |
| 2007/0142885 | A1* | 6/2007 | Hantash | A61N 1/06 607/102 |
| 2008/0208179 | A1* | 8/2008 | Chan | A61B 18/203 606/9 |
| 2008/0269735 | A1* | 10/2008 | Vila Echague | A61B 18/20 606/15 |
| 2009/0069741 | A1* | 3/2009 | Altshuler | A61B 5/441 604/22 |
| 2010/0082019 | A1 | 4/2010 | Neev | |
| 2011/0150924 | A1* | 6/2011 | Della Rocca | A61K 39/39 424/204.1 |
| 2011/0218464 | A1* | 9/2011 | Iger | A61B 18/14 601/2 |
| 2012/0143056 | A1* | 6/2012 | Slayton | A61B 8/14 600/439 |
| 2012/0150266 | A1* | 6/2012 | Shalev | A61N 1/20 607/99 |
| 2013/0066237 | A1* | 3/2013 | Smotrich | A61N 5/0619 601/2 |

OTHER PUBLICATIONS

Manstein, D et al., Fractional Photothermolysis: A New Concept for Cutaneous Remodeling Using Microscopic Patterns of Thermal Injury, Laser Surg. Med. 2004, vol. 34, No. 5, pp. 426-438, abstract, p. 427, col. 1, paragraph 2, p. 427, col. 2, paragraph 5, figure 1c, Table 1, p. 428, col. 2, paragraph 1.*

International Search Report and Written Opinion dated Jul. 24, 2014 for International Application No. PCT/US2014/025659.

Lee, WR et al. Laser-Assisted Topical Drug Delivery by Using a Low-Fluence Fractional Laser: Imiquimod and Macromolecules, Journal of Controlled Release, Aug. 10, 2011, vol. 153, No. 3, pp. 240-248, abstract, p. 240, col. 1, paragraph 2, p. 241, col. 1, paragraphs 1, 5.

Wilck, MB et al., Safety and Immunogenicity of Modified Vaccinia Ankara (ACAM3000): Effect of Dose and Route of Administration, J. Infect. Dis., May 1, 2010, vol. 201, No. 9, pp. 1361-1370, abstract, p. 1368, col. 1, paragraph 2.

Lee, B. et al., A Predictive Model of the Economic Effects of an Influenza Vaccine Adjuvant for the Older Adult (Age 65 and Over) Population, Vaccine, Apr. 6, 2009, vol. 27, No. 16, pp. 2251-2257, abstract, p. 2251, col. 1, paragraphs 3-4.

* cited by examiner

C

METHOD AND APPARATUS FOR BOOSTING VACCINE EFFICACY

CROSS-REFERENCE TO RELATED APPLICATIONS

This application is a 371 application of PCT/US2014/025659 filed Mar. 13, 2014 which claims priority based on U.S. Provisional Patent Application No. 61/789,775 filed Mar. 15, 2013.

STATEMENT REGARDING FEDERALLY SPONSORED RESEARCH

This invention was made with government support under grant numbers AI089779, AI070785, AI097696, and DA028378 awarded by the National Institutes of Health. The government has certain rights in the invention.

FIELD OF THE INVENTION

The present invention is directed to a method and apparatus for increasing the efficacy of various vaccines. Such enhancement can be achieved using a method and apparatus that include generating a plurality of small (for example, sub-millimeter) regions of tissue preparation in the vaccination site to increase the local population of antigen-presenting cells prior to introduction of the vaccine.

BACKGROUND

Flu viral infection continues to be a significant public health problem, and vaccination is one of the most cost-effective means to prevent the spread of the virus and decrease flu-caused morbidity and mortality. However, annual flu vaccination presents a huge burden, economically, clinically and in production efforts, for the public health system. In particular, when an outbreak of a new strain or pandemic of flu virus occurs, manufacturers face an enormous challenge to double or triple the production of flu vaccines in order to cope with both seasonal and pandemics of flu virus. A method and system that provides dose-sparing of existing and stockpiled vaccines can greatly enhance a capacity to cope with flu vaccine shortages in the event of a flu pandemic, and could result in huge cost savings for seasonal flu vaccines. In addition, vaccine enhancement can provide further benefits such as improving the efficacy of vaccines in the elderly and immunocompromised patients.

Most vaccines may benefit from adjuvants to induce sufficient immune responses in the human body. An "adjuvant" can refer to any aid or contributor that can increase the efficacy or potency of a vaccine for the prevention, amelioration, or cure of a disease as compared to a vaccine or agent administered without the adjuvant. For example, an increase in the efficacy or potency can include a decrease in the amount of vaccine or agent to be administered, a decrease in the frequency and/or number of doses to be administered, a reduction in the likelihood and/or severity of undesirable side effects of the vaccine, and/or a more rapid or robust response to the vaccine (e.g., a higher antibody titer).

Currently, very few chemical or biological vaccine adjuvants are approved for human use in the Western Hemisphere. Aluminum salts (aluminum hydroxide, aluminum phosphate or alum) have been used in vaccine preparations for a long time. These salts can create more antigenic precipitates with some vaccines, or increase the local concentration of antigen at the injection site to enhance vaccine uptake by antigen-presenting cells, among other possible effects. However, aluminum salts can also cause side effects in a percentage of the population that receives such vaccinations and may be undesirable for skin vaccination due to severe skin irritation it can cause. Certain other adjuvants are undergoing stringent approval testing in various countries, but have yet to gain wide acceptance.

In general, safety of vaccines (and associated adjuvants) is considered to be critical because vaccines are used to prevent illness, not to treat a disease. Any potential risks or unwanted side effects of a vaccine must be weighed against the reduction in likelihood of contracting the actual disease they are designed to treat, and the health risks of such disease if contracted. Accordingly, finding safe and effective vaccine adjuvants is becoming increasingly important.

One approach to produce an adjuvant by exposing the injection site to laser light having certain characteristics is described, e.g., in U.S. Patent Application Publication No. 2011/0059116 of Onikienko et al. The described method appears to stress the cells to release immunostimulatory factors such as heat shock proteins that can improve vaccine efficacy. However, the method requires certain narrow combinations of wavelengths, pulse power, and pulse durations to evoke the desired effects while avoiding significant irreversible damage (e.g., necrosis or aptosis) to skin cells exposed to the laser energy (for example, limiting irreversible damage to 1% or less than of the exposed cells). Such limitations on the parameters of the laser energy that can produce the desired effects may include limitations based on skin color or pigmentation, and thus may limit the application of such methods based on clinical skill and/or within certain populations.

Fractional resurfacing, or fractional photothermolysis, is a dermatological technique in which small regions of skin tissue (epidermis and/or dermis) are thermally damaged or ablated using electromagnetic energy (generally optical energy from a laser, flashlamp, laser diode, etc.) to stimulate a healing response in the skin. An example of a "fractional" approach to skin resurfacing is described, e.g., in U.S. Patent Publication No. 2006/0155266 of Manstein et al. In fractional resurfacing, the width of the skin regions exposed to energy is typically less than 1 millimeter, or even less than 0.5 millimeters. Such small damage zones, which can extend to the dermal layer, are well-tolerated by the skin, partially because the small regions of damage remain surrounded by healthy tissue. Fractional photothermolysis can produce effects such as skin tightening, wrinkle reduction, and improvement in pigmentation appearance. Fractional photothermolysis can be ablative (where a portion of the skin tissue is vaporized in the exposed regions), or non-ablative (where skin tissue is thermally damaged but not vaporized). For example, non-ablative fractional photothermolysis (NAFP) maintains a substantially intact stratum corneum and reduces a risk of infection as compared to other skin resurfacing techniques.

Other dermatological treatments have been developed based on the fractional damage concept. Various modalities for heating, ablating, or otherwise disrupting small regions of tissue (e.g., less than 1 millimeter wide or less than 0.5 millimeters wide) can be used to achieve various cosmetic effects. Generally, formation of small regions of thermal damage in tissue that are surrounded by healthy, unaffected tissue (e.g., fractional thermolysis) is generally well-tolerated.

Accordingly, it may be desirable to provide methods and apparatus for enhancing the efficacy of various vaccines that are not vaccine-specific and which are well-tolerated by the subject.

SUMMARY OF THE DISCLOSURE

Embodiments of the present invention provide a method, system and apparatus for enhancing the efficacy of various vaccines by using, e.g., fractional thermolysis techniques and variations thereof, to generate a plurality of discrete microscopic regions of damaged tissue in a target zone of skin tissue, and then administering the vaccine into the target zone. For example, the damage can be generated thermally using, e.g., optical energy, radio frequency (rf) energy, other forms of electromagnetic energy, ultrasound energy, resistive heating, or the like to form microscopic thermal zones (MTZs) in the tissue. For example, a width of the MTZs can be less than about 1 millimeter, or less than 0.5 millimeters. A fractional areal coverage of the target zone by the MTZs is, for example, between about 5% and 40%. Certain topical adjuvants, such as Imiquimod (1-(2-Methylpropyl)-1H-imidazo[4,5-c]quinolin-4-amine, an immune response modifier) or the like, can be applied to the target zone to increase the vaccine efficacy further. As used herein and in the drawings, Imiquimod may be likewise referred to as IMIQ.

In one aspect, the invention provides a method of vaccinating a mammalian subject. The method includes the steps of: arranging a source of electromagnetic radiation proximate to a target zone of skin of the mammalian subject; controlling the source of electromagnetic radiation to deliver a dose of electromagnetic radiation to the target zone determined to create at least one thermally-denatured zone in the target zone; and intradermally injecting a vaccine within the target zone to vaccinate the mammalian subject. In one form, a width of one or more of the thermally denatured zones is less than about 1 millimeter. The thermally denatured zone may comprise columns having thermally denatured epidermal and dermal tissue and a stratum corneum that is not denatured, and wherein the columns are spatially separated from one another by an unirradiated area of skin. A fractional surface coverage of the target zone by the denatured zone(s) may be between 5% and 40%. The width of the columns may be about 0.1 millimeters. The source of electromagnetic radiation may includes at least one of a non-ablative laser, a diode laser, a fiber laser, a flashlamp, and a solid state laser. The electromagnetic radiation source can be a non-ablative laser. The method may further comprise applying an immune response modifier, such as Imiquimod, to the target zone.

In one version of the method, Hemagglutination inhibition (HAI) antibody titer in the mammalian subject is increased following vaccination compared to HAI antibody titer in a mammalian subject intradermally injected with the vaccine but not receiving the dose of electromagnetic radiation to produce the at least one thermally denatured zone.

In another version of the method, IgG antibody titer in the mammalian subject is increased following vaccination compared to IgG antibody titer in a mammalian subject intradermally injected with the vaccine but not receiving the dose of electromagnetic radiation to produce the at least one thermally denatured zone. The IgG antibody titer may be IgG2a antibody titer.

In another version of the method, the helper T cell immune response in the mammalian subject is increased following vaccination compared to the helper T cell immune response in a mammalian subject intradermally injected with the vaccine but not receiving the dose of electromagnetic radiation to produce the at least one thermally denatured zone. The helper T cell may be a Th1 helper T cell. The helper T cell may be a Th2 helper T cell.

In one version of the method, the vaccine is selected from the group consisting of a pneumococcal vaccine, a meningococcal vaccine, a hepatitis vaccine, a chickenpox vaccine, a diphtheria vaccine, a *haemophilus* influenza vaccine, an influenza vaccine, a measles vaccine, a mumps vaccine, a pertussis vaccine, a polio vaccine, a rotavirus vaccine, a rubella vaccine, a shingles vaccine, a respiratory syncytial virus vaccine, a human papillomavirus vaccine, and a tetanus vaccine. The method can provide at least a 5-fold dose-sparing of the vaccine. The method can overcome age-related immunosenescence.

In another aspect, the invention provides a system for enhancing the efficacy of a vaccine. The system includes a fractional arrangement configured to generate at least one region of thermal denaturation in a target zone of biological tissue; and a delivery arrangement configured to deliver a dose of the vaccine into the target zone. A width of the region(s) is less than about 1 millimeter, and each region is surrounded by substantially undamaged tissue. The fractional arrangement and the delivery arrangement can be provided in a single housing.

The fractional arrangement and the delivery arrangement can be provided in separate housings. The fractional arrangement can include a marking arrangement provided on a lower surface thereof, wherein the marking arrangement is configured to provide a visible marker on or proximal to the target zone to facilitate accurate placement of the delivery arrangement on the target zone. The system can further include a locating arrangement configured to be adhered to the target zone, wherein each of the fractional arrangement and the delivery arrangement are configured to be removably coupled to the locating arrangement. The fractional arrangement can include an immune response modifier delivery system provided on a lower surface thereof, wherein the delivery system is configured to provide an immune response modifier on or proximal to the target zone.

The fractional arrangement can include a source of optical energy. The fractional arrangement can include a plurality of needles configured to contact or penetrate into the target zone, and a source of radio frequency (rf) or thermal energy configured to be directed to the needles to generate the at least one region of thermal denaturation. The fractional arrangement can include a source of ultrasound energy configured to generate the at least one region of thermal denaturation. The delivery arrangement can be at least one of a needle, a fractional patch, a microneedle-array patch, or a microproject-array patch.

In the system, the vaccine can be selected from the group consisting of a pneumococcal vaccine, a meningococcal vaccine, a hepatitis vaccine, a chickenpox vaccine, a diphtheria vaccine, a *haemophilus* influenza vaccine, an influenza vaccine, a measles vaccine, a mumps vaccine, a pertussis vaccine, a polio vaccine, a rotavirus vaccine, a rubella vaccine, a shingles vaccine, a respiratory syncytial virus vaccine, a human papillomavirus vaccine, and a tetanus vaccine.

In another aspect, the invention provides a system for vaccinating a subject. The system can include an electromagnetic radiation source configured to be arranged proximate to a target zone on an exterior of the subject; a user control configured to selectively cause the electromagnetic radiation source to deliver a dose of electromagnetic radiation toward the target zone to create at least one thermally-denatured zone in the target zone; and a vaccine-delivery system configured to deliver a vaccine to the target zone. A width of the thermally-denatured zone(s) is less than about 1 millimeter, and each thermally-denatured zone can be surrounded by substantially undamaged tissue.

The electromagnetic radiation source, the user control, and the vaccine-delivery system can be provided in a single housing. The housing can include a masking arrangement provided on a lower surface thereof, wherein the masking arrangement includes at least one optically transparent opening. The masking arrangement can include a channel for receiving a needle of the vaccine-delivery system.

Alternatively, the electromagnetic radiation source can be provided in a first housing and the vaccine-delivery system can be provided in separate second housing. The first housing can include a marking arrangement provided on a lower surface thereof, wherein the marking arrangement is configured to provide a visible marker on or proximal to the target zone to facilitate accurate placement of the vaccine-delivery system on the target zone. The first housing can include a masking arrangement provided on a lower surface thereof, wherein the masking arrangement includes at least one optically transparent opening. The masking arrangement can include a channel for receiving a needle of the vaccine-delivery system. The system can further include a locating arrangement configured to be adhered to the target zone, wherein each of the first housing and the second housing are configured to be removably coupled to the locating arrangement. The locating arrangement can include a channel for receiving a needle of the vaccine-delivery system. The locating arrangement can include at least one optically transparent opening.

In the system, the electromagnetic radiation source can be a source of optical energy configured to generate the at least one thermally-denatured zone. The electromagnetic radiation source can be a source of ultrasound energy configured to generate the at least one thermally-denatured zone. The electromagnetic radiation source can be a non-ablative laser. The system can further include an immune response modifier delivery system configured to provide an immune response modifier on or proximal to the target zone. The immune response modifier can be Imiquimod.

In the system, the vaccine can be selected from the group consisting of a pneumococcal vaccine, a meningococcal vaccine, a hepatitis vaccine, a chickenpox vaccine, a diphtheria vaccine, a *haemophilus* influenza vaccine, an influenza vaccine, a measles vaccine, a mumps vaccine, a pertussis vaccine, a polio vaccine, a rotavirus vaccine, a rubella vaccine, a shingles vaccine, a respiratory syncytial virus vaccine, a human papillomavirus vaccine, and a tetanus vaccine.

These and other features of the present invention will become apparent upon reading the following detailed description of embodiments of the invention, when taken in conjunction with the appended claims.

BRIEF DESCRIPTION OF THE DRAWINGS

Further features of the invention will become apparent from the following detailed description taken in conjunction with the accompanying figures showing illustrative embodiments, results and/or features of the exemplary embodiments of the present invention, in which.

Figure 1:
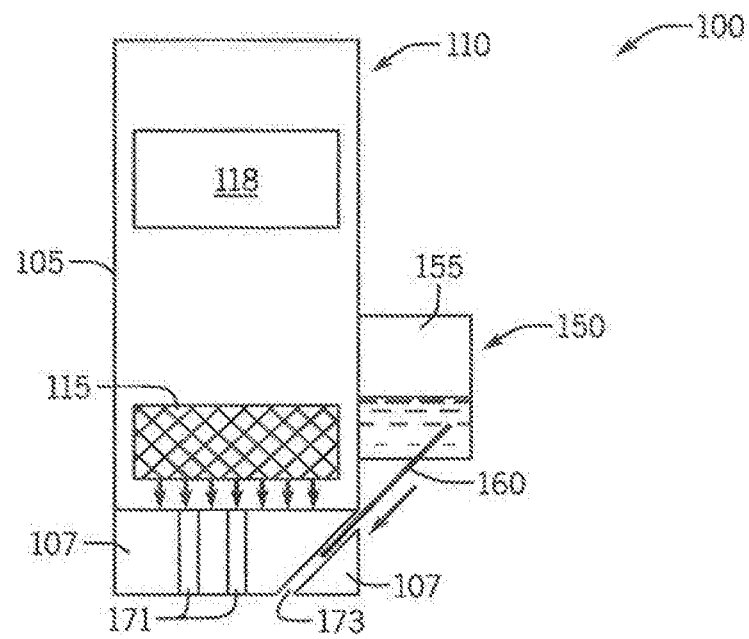
FIG. 1 is a schematic illustration of an exemplary apparatus in accordance with exemplary embodiments of the present disclosure.

Throughout the drawings, the same reference numerals and characters, unless otherwise stated, are used to denote like features, elements, components, or samples of the illustrated embodiments. Moreover, while the present invention will now be described in detail with reference to the figures, it is done so in connection with the illustrative embodiments and is not limited by the particular embodiments illustrated in the figures.

DETAILED DESCRIPTION OF EMBODIMENTS OF THE DISCLOSURE

Recent public concerns about safety of adjuvantated influenza (flu) vaccine stress the urgent need of a safer adjuvant.

We describe herein augmentation of flu vaccine in adult and old mice and in pigs by micro sterile inflammation, without involving injection of any adjuvant.

In one non-limiting illustrative example, the inoculation site was first illuminated for 1 second with an over-the-counter laser before flu vaccine was intradermally injected. Then, Imiquimod cream (IMIQ), an agonist for Toll-like receptor 7, was topically applied to the inoculation site. Non ablative fractional laser (NAFL) created an array of micro-thermal zones (MTZs) beneath the stratum corneum at the inoculation site, and the dying cells in each MTZ sent "danger" signals, provoking the production of various chemokines that attracted a large number of antigen presenting cells (APCs), in particular, plasmacytoid dendritic cells (pDCs) around each MTZ forming a micro-sterile inflammation array. The recruited pDCs were activated by IMIQ diffusing from the skin surface and secreted a high level of pro-inflammatory cytokines leading to a strong Th1 immune response. The Th1 immunity was abrogated significantly by systemic depletion of pDCs, a local TNF-$\alpha$ inhibitor, or in the absence of IFN regulatory factor 7 (IRF7), highlighting a pivotal role of this regulatory pathway in the adjuvanicity. In contrast to conventional adjuvants that stimulate persistent inflammation and severe skin lesion, NAFL/IMIQ caused little overt inflammation in the skin while sufficiently enhancing flu vaccine-mediated immune responses and hindering skin irritation evoked by flu vaccines. The micro-sterile inflammation strategy confers a means to improve the efficacy of flu vaccines, yet with diminished local and systemic adverse events.

Tremendous progress has been made in the past decade in understanding of sterile inflammation, which is a natural response to invaders or injury in protection of our body and induced by danger signals released from dying cells. The danger signals, named damage-associated molecular patterns (DAMPs), include uric acid, dsDNA and others, and can attract and activate antigen presenting cells (APCs). The sterile inflammation is one of the primary mechanisms behind alum and MF59 adjuvants, two licensed vaccine adjuvants and forms the basis for today's adjuvant development. The ability of sterile inflammation to boost immune responses against vaccines raises an intriguing possibility that skin injury can serve as safe "adjuvant" for cutaneous vaccination, provided that the injury is well under control. Non-ablative fractional laser (NAFL) can be such a great technology to controllably injure the skin at the site of vaccine inoculation. The laser treatment generated an array of micro-thermo zones (MTZs) in a desirable number, size, and depth without damaging skin's outer protective barrier, so that the skin barrier function is well preserved. Each MTZ is so small that it can be healed within one or two days by fast growing epithelial cells surrounding each MTZ, resulting in younger-looking skin. Indeed skin renewing by NAFL has been a cosmetic industry for decades. The micro-skin injury sharply contrasts the injury induced by intradermal (ID) injection of adjuvants that often evoke severe and persistent inflammation and severe skin lesion and is not acceptable for routine vaccination.

We hypothesized that laser-injured cells within the MTZs could send danger signals to induce sterile immunity and serve as a safe adjuvant for cutaneous vaccines. Skin is prone to adjuvant-induced inflammation and tends to cause more severe local reactogenicity including erythema, swelling, and ulceration that are persistent for weeks. Because of this unwanted adverse events, most current adjuvants such as Alum, oil-in-water emulsion adjuvants, and several TLR agonists are not suitable for skin vaccination. Adjuvant for cutaneous vaccination remains the urgent need for future needle-free vaccinations and for the ID immunization that is more potent than the conventional intramuscular (IM) immunization as shown by a number of studies.

We present herein that NAFL induces sterile inflammation at a micro-scale which causes no overt skin lesion while greatly augmenting flu vaccines ID administered. The danger signals released by dead cells in laser-generated MTZs preferably attracted plasmacytoid dendritic cells (pDCs) that were subsequently activated by topically applied Imiquimod (IMIQ) cream, leading to synergistic augmentation of the immune response against influenza (flu) vaccine in adult and old mice and in pigs, strikingly concomitant with improved local and systemic safety profiles.

The present invention relates to a method and apparatus for enhancing the efficacy of intradermal vaccines and increase subsequent immunological responses by generating a fractional pattern of thermal preparation regions, or micro-thermal zones (MTZs), at a target injection or administration site using optical energy, prior to introducing a vaccine into the target site. The MTZs can be generated using various arrangements, including ablative fractional photothermolysis (AFP) and non-ablative fractional photothermolysis (NAFP) methods and devices, ultrasound arrays, arrays of rf needle electrodes, or resistance-heated needles, etc. The vaccine is preferably administered after the MTZs have been formed in the injection site, which can avoid damage or modification to the vaccine components/compounds by any of the various forms of energy used to generate the MTZs. For example, the vaccine can be introduced immediately after formation of the MTZs, up to, for example, about 24 hours after their formation.

Without being bound by a particular theory, it has been observed that an increased number of antigen-presenting cells (APCs) tend to surrounding MTZs after they are generated in the skin. The MTZ-mediated enrichment of APCs can boost immune responses elicited by various vaccines administered intradermally. Fractional thermolysis treatment of a vaccine administration site can also enhance the motility of APCs and speed up their migration from the skin to draining lymph nodes. Further, fractional thermolysis pre-treatment of a vaccine administration site can augment immune responses against various vaccines independently of skin color while causing little skin damage visibly or histologically.

An exemplary vaccine apparatus 100 in accordance with exemplary embodiments of the present disclosure is illustrated in FIG. 1. The apparatus 100 includes a fractional arrangement 110 configured to generate a plurality of MTZs in a target zone of a biological tissue, and a delivery arrangement 150 configured to deliver a dose of a vaccine or similar substance into the tissue target zone. In general operation, the apparatus 100 can be placed against or onto the target zone, the fractional arrangement 110 can then be activated to generate the MTZs in the target zone, and the delivery arrangement 150 then be activated to deliver the vaccine into the target zone.

In certain embodiments, the fractional arrangement 110 can include a source of energy 115 such as, e.g., a laser, a flashlamp, one or more lasers diodes, a patterned ultrasound generator, a plurality of needle electrodes, or the like. The apparatus 100 can include a source of power for the energy source 115 provided within a housing 105, or it can be connected to an external power source such as an electrical outlet. In further embodiments, the apparatus 100 can receive optical energy from an external source such as, e.g., laser energy generated by an external laser device (not shown) and delivered to the apparatus 100 via one or more optical fibers, waveguides, or the like (also not shown).

The fractional arrangement 110 can further include a control arrangement 118 configured to control aspects of the energy provided by the fractional arrangement 110 to form a plurality of MTZs on the target zone. In certain embodiments, the energy source 115 can provide optical energy, e.g., from a laser, flashlamp or the like, and the control arrangement 118 can include a plurality of lenses, a mechanical actuator, a movable mirror or prism, and/or a translator adapted to direct a beam or a series of pulses of the optical energy onto discrete locations in the target zone. The optical energy can be either ablative or nonablative. For example, the optical energy source can include a $CO_2$ laser, a fiber laser, one or more diode lasers, an Er:YAG laser, or any other type of laser or optical energy source that can be used to generate fractional thermal damage in biological tissue. The control arrangement 118 can further include control circuitry to control an output of the energy source 115, e.g., to generate a plurality of timed pulses that coordinate with a translator, deflector, mirror, etc. to direct the pulses of energy onto particular locations on the target zone.

In further embodiments, the energy source 115 can be a flashlamp, a combustion lamp or the like, and the control arrangement 118 can work in conjunction with a plate 107, which can include a mask having a plurality of holes or other optically transparent openings therethrough provided between the energy source 115 and the target zone of tissue to be treated. Portions of the generated light can pass through the holes in the mask to irradiate portions of the target zone and generate MTZs, while the mask blocks light from irradiating tissue beneath the mask between the openings.

In still further embodiments, the energy source 115 can be a focused ultrasound device configured to direct a plurality of ultrasound pulses onto the target zone, and the control arrangement 118 can include circuitry, a translator, etc. configured to control the pattern of ultrasound energy applied to the tissue to form a plurality of MTZs.

In additional embodiments of the disclosure, the energy source 115 can include a plurality of small needles 180 configured to contact the surface of the target zone tissue or, alternatively, penetrate the tissue to a particular depth, when the apparatus 100 is placed on the target tissue. In further embodiments, the plurality or array of needles 180 can be configured to advance onto or into the tissue after the apparatus 100 has been placed on the tissue surface. In some embodiments, energy in the form of, e.g., rf energy (in monopolar or bipolar mode) can be directed into the needles 180 contacting or penetrating the target zone to form discrete MTZs therein. In still further embodiments, thermal energy provided by a resistance heater or the like can be conducted through the needles 180 to form MTZs in the target zone.

In general, the fractional arrangement 110 can be configured to direct energy, using any of the various modes described herein, onto or into a plurality of discrete locations on the target zone, to form MTZs that are, for example, less than about 1 millimeter wide, or less than 0.5 millimeters wide. The fractional areal coverage of the target zone by the MTZs can be, e.g., between about 5% and about 40%. This range of surface coverage can provide a sufficiently high volumetric amount of thermal preparation, such as denaturing or thermal damage in the target zone to achieve the desired effects described herein, while also preserving enough healthy tissue between the MTZs to facilitate rapid healing of the target zone and promote motility of the antigen-presenting cells and any other beneficial mechanisms that may operate to improve the vaccine efficacy. The target zone can be circular or square in shape, although other shapes can also be used. It can be between about 0.5 centimeters and 2 centimeters wide. This size range is generally large enough to provide a sufficient degree of local thermal damage in the skin tissue to achieve the beneficial results described herein, while not being so large as to create a target zone of thermally-treated tissue than is needed to enhance a dose of vaccine. In certain embodiments, the target zone can be somewhat larger or smaller than this exemplary range. For example, the target zone may be larger if a particular vaccine requires a relatively large volume of vaccine to be administered.

In embodiments where the fractional arrangement 110 provides optical energy to form the MTZs, each discrete location on the target zone can be irradiated with between, for example, about 1 mJ and 100 mJ of optical energy to form each of the MTZs. Such energy levels can be provided, e.g., by suitable configuration of the control arrangement 118 and/or control of the energy source 115.

The optical energy can have a wavelength greater than, for example, around 800 nanometers. For example, the optical energy can have a wavelength in any of the following examples of ranges: 1,200 to 1,600 nanometers, 1,850 to 2,100 nanometers, or 2,300 to 3,100 nanometers. Such wavelengths are often used in conventional NAFP devices and systems, as they are preferably absorbed by water as compared to pigment in the skin, such that the NAFP procedure will be relatively insensitive to pigmentation characteristics of the target zone. In some embodiments, the fractional arrangement 110 can deliver optical energy, for example, at 532 nanometers or 1410 nanometers to form MTZs in the target zone. In certain embodiments, optical energy containing a plurality of wavelengths can be used (e.g., the output of a flashlamp or combustion lamp).

In general, the control arrangement 118 can include control circuitry, switches, actuators, and/or other components configured to control an output of the energy source 115 for any of the energy modalities described herein, such that the energy source 115 will generate a plurality of MTZs having desired properties (e.g., percent of surface coverage, total energy per MTZ, etc.) in the target zone when activated.

The delivery arrangement 150 can include a reservoir 155 that contains the vaccine to be administered. For example, the reservoir 155 can be a removable and disposable vial that contains a single dose. In further embodiments, the reservoir 155 can be a container that holds a plurality of doses, where the delivery arrangement 150 is configured to deliver a single dose into the target zone when activated.

The delivery arrangement 150 further includes a needle 160 or other delivery conduit to direct the vaccine into the target zone. For example, the delivery arrangement 150 can include a fractional patch (such as a power-made patch), a microneedle-array patch, a microproject-array patch that contains vaccines printed in the same pattern as the pattern of MTZs on the target area, etc. to deliver the vaccine into the target zone. The microneedle or microproject-array can include biocompatible and/or dissolvable microneedles that can be formed using one or more vaccine compounds and various polymers. Other arrangements known in the art for delivering vaccines and similar substances into biological tissues can also be used in embodiments of the present disclosure. Certain components of the delivery arrangement 150, including but not limited to the reservoir 155, the needle 160, or the various patches can be disposable, e.g., they can be provided as a cartridge or other type of replaceable unit in the device.

The delivery arrangement 150 can be configured to deliver a dose of the vaccine into the target zone after the MTZs have been formed therein. For example, the needle 160 (if present) can be positioned to advance and penetrate a location within the target zone and inject the vaccine dose, as illustrated in FIG. 1. The delivery arrangement 150 can include a manual plunger or actuator to inject or administer a vaccine dose into the target zone. In further embodiments, the delivery arrangement 150 can include an automatic delivery system, e.g., it can be powered by electricity, hydraulic pressure, etc., and can be configured to direct a single dose into the target zone when activated, even if the reservoir 155 or other vaccine delivery component holds a larger quantity of the vaccine.

A lower portion of the housing 105 can be configured to be placed on or directly over the target zone, such that the delivery of energy by the fractional arrangement 110 and delivery of vaccine by the delivery arrangement 150 are each directed onto the target zone. In certain embodiments, the lower portion of the housing 105 can include a plate 107 configured to be placed over the target zone and allow passage of energy therethrough. For example, the plate 107, if present, can be optically transparent to the relevant wavelength(s) if the energy source 115 is configured to deliver optical energy onto the target zone to form MTZs. The plate 107 can include a plurality of holes 171 or openings therethrough that allow a plurality of needles to pass therethrough, if the energy source is configured to deliver rf or resistive heat energy through a needle array as described above. The plate 107 and energy source 115 can be configured to control the penetration depth of the plurality of needles into the target zone.

The plate 107, if present, can further include one or more channels 173 therethrough positioned to allow the needle 160 to pass therethrough, and to guide the needle 160 onto the target zone. In further embodiments, the lower portion of the housing 105 can include an opening configured to be placed over the target zone such that energy and the vaccine dose (from the fractional arrangement 110 and the delivery arrangement 150, respectively) are directed into the target zone. The plate 107 (or lower surface of the housing 105 if no plate 170 is present) and delivery arrangement 150 can be configured to control the penetration depth of the needle into the target zone. For example, these components can be configured such that the needle penetrates the target zone to a depth between about 0.5 and 2.5 millimeters to inject the vaccine. Microneedle arrays, if used, may penetrate to a similar or shallower depth. In this manner, the injection depth of the vaccine can be more precisely controlled than with an unsupported hypodermic needle.

Although a specific configuration of the components of the apparatus 100 are shown in FIG. 1, other configurations and variations can be provided in further embodiments of the present disclosure, where the different configurations are also adapted to form MTZs and then administer a dose of vaccine into a common target zone.

In certain embodiments, the fractional arrangement 110 and the delivery arrangement 150 can each be activated separately. In further embodiments, both the fractional arrangement 110 and the delivery arrangement 150 can be activated by a single switch, such that the fractional arrangement 110 forms MTZs in the target zone prior to administration of the vaccine dose by the delivery arrangement 150.

In a further embodiment, shown in FIGS. 2A-2B, an enhanced vaccination system 200 can be provided as a kit that includes a separate fractional arrangement 110 and delivery arrangement 150. Formation of MTZs and subsequent delivery of vaccine into the same target zone containing the MTZs is desirable to achieve the highest vaccine enhancement benefits described herein. Accordingly, precise alignment of the fractional arrangement 110 and delivery arrangement 150 is generally desirable when using the system 200. The system 200 can include a locating arrangement 250 to facilitate accurate delivery of the optical energy and the vaccine dose into a small target zone. The locating arrangement 250 can be a small plate, disc, ring, or other object that can be temporarily adhered to the tissue surface on or around the target zone. The lower portion of the housing 205 of the fractional arrangement 110 can be adapted to align or engage with the locating arrangement 250, as shown in FIG. 2A, such that the fractional arrangement 110 generates a plurality of MTZs in the target zone. A lower portion of the delivery arrangement 150 can also be configured to align or engage with the same locating arrangement 250, as shown in FIG. 2B, such that the delivery arrangement 150 delivers a dose of vaccine into the same target zone when activated. The locating arrangement 250 can be removed from the tissue surface after the vaccine dose is administered. This exemplary system can facilitate accurate positioning of both the fractional arrangement 110 and the delivery arrangement 150 over the same target zone, to improve the ease and accuracy of the spatial positioning of the MTZ generation process and vaccine dose administration.

In a further embodiment, not illustrated in the figures, the fractional arrangement 110 and delivery arrangement 150 can also be provided as separate arrangements. A lower portion of the housing 205 of the fractional arrangement 110 can include a marking arrangement such as, e.g., an ink stamp or the like, that is configured to contact the surface of the target zone and outline the target zone. The delivery arrangement 150 can be a conventional syringe or the like. In typical use, this fractional arrangement 110 can be placed over the target zone and activated to form a plurality of MTZs within the target zone. The fractional arrangement 110 can then be removed from the target zone, where the marking arrangement 210 leaves an identifying marker on the tissue surface, e.g., to delineate the location of the treated target zone. The delivery arrangement 150 can then be directed onto the marked target zone and activated to deliver a vaccine does into the target zone.

In further embodiments, certain immune modifiers, such as agonists of toll-like receptors (TLRs), can be applied topically to the target zone and may synergistically augment the immune-enhancement mediated by the NAFP procedure. For example, it has been observed that NAFP can reduce skin irritation often caused by intradermal administration of influenza vaccines. NAFP followed by topical application of an immune response modifier, such as Imiquimod cream (5%), which is an agonist of toll-like receptor 7 (TLR-7), to the target zone did not worsen skin reaction induced by influenza vaccines but has been observed to further boost the associated immune responses. Such topical compounds can be applied to the target zone, e.g., manually, in a bandage or patch applied to the target zone, as a coating transferred from a portion of any exemplary apparatus or system described herein that contacts the target zone, etc. For example, a topical compound can be provided as a coating or layer on the lower portion of the housing 105 or plate 107 of apparatus 100, the lower portion of the housing 205 and/or the locating arrangement of system 200, etc.

Accordingly, systems and methods according to the present disclosure can both boost immune responses and reduce undesirable side effects. Further, in contrast to many vaccine adjuvants that alter a physical or chemical form of a given vaccine, NAFP is not vaccine-specific and can "prime" the body to generate improved responses to the vaccine. Accordingly, embodiments of the present disclosure can be used to boost any of a wide range of vaccine types.

In still further embodiments, the exemplary methods, apparatus and systems described herein can be used to deliver thermal energy to form MTZs and administer vaccines in target zones other than the surface of skin such as, e.g., mucosal areas to enhance efficacy of mucosal vaccinations or intramuscularly. For example, a catheter or fiber optic arrangement can be adapted to deliver optical energy to the nostril, the genital areas, the anus, muscle tissue, or other vaccination sites in the body in a pattern as described herein.

A number of exemplary studies of methods and observed results in accordance with embodiments of the present disclosure are presented below. Such examples, although not limited to the specific features described therein, can also be adapted to be used with the exemplary systems and devices described herein. In these Examples, "Laser" refers to treatment of the target zone with NAFP as described in the specific examples, although other energy modalities could also be used to form the MTZs in similar examples and applications.

EXAMPLES

Example 1

Laser/Imiquimod Improves Humoral and Cell-Mediated Immune Responses

The potency of Laser/Imiquimod creme (IMIQ, 3M Pharmaceuticals) adjuvant to enhance pandemic vaccine-induced humoral immune response was evaluated. Mice were intradermally immunized with 2009 H1N1 pandemic vaccine alone or in the presence of Laser, Imiquimod, or Laser/Imiquimod adjuvant. Four weeks later, serum HAI and specific antibody titer were quantified.

Figure 4:
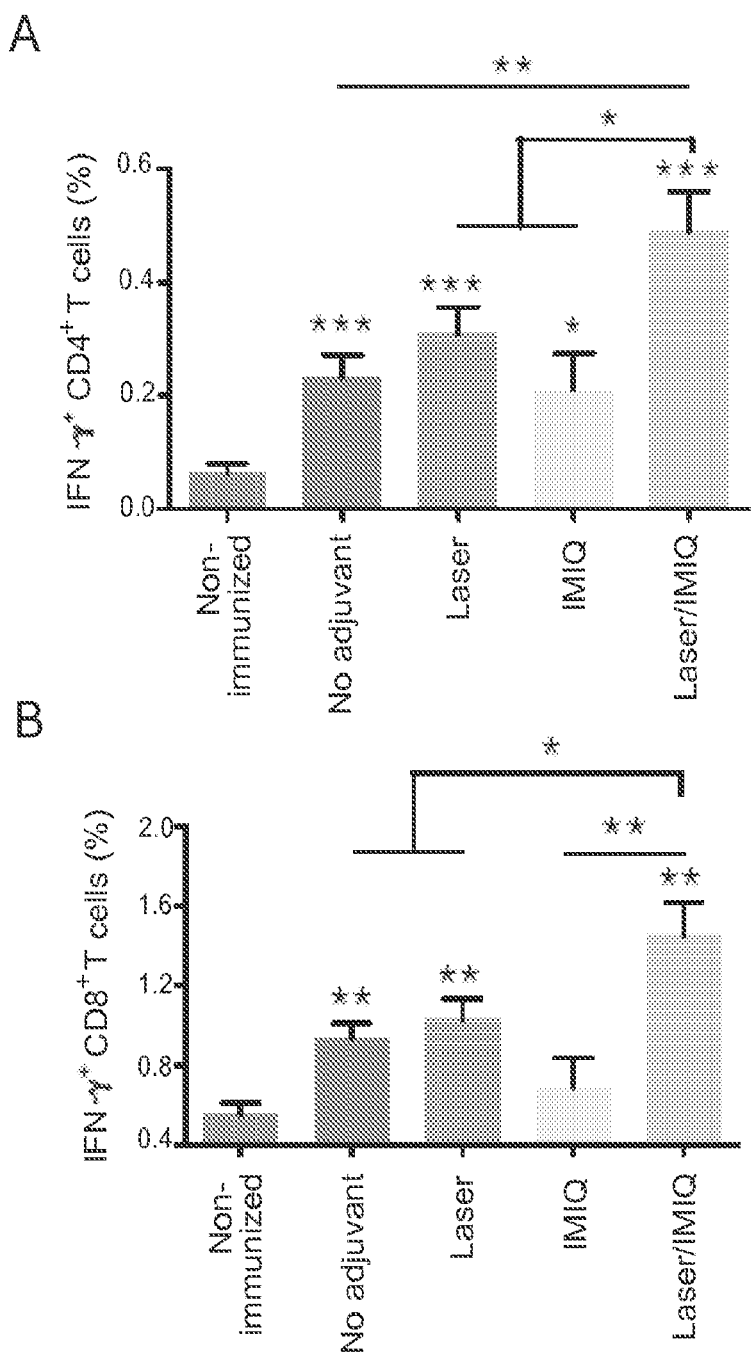
FIGS. 4A and 4B are graphs that evidence increases in pandemic vaccine-induced cellular immune response following treatment of the target zone with NAFP and/or Imiquimod.

Young adult BALB/c mice (male, 6-8 weeks) were purchased from Charles River Laboratories. Old BALB/c mice (male, 18 months) were obtained from National Institute of Aging (NIA). Animals were housed in the animal facilities of Massachusetts General Hospital (MGH) and all procedures were in compliance with institutional, hospital, and NIH guidelines. A laser device was used that emits a 1410-nanometer laser light with 0.15 mrad beam divergence and 10 ms pulse duration, except as otherwise specified. One treatment using this device generates a 5×8 array of microthermal zones (MTZs) in a 7×10 $mm^2$ area. In the current study, two treatments at the medium power were used to generate overlapped MTZs in the same target zone. Pandemic influenza virus A/California/7/2009 (H1N1) was obtained from American Type Culture Collection (ATCC, #FR-201). Influenza viruses were expanded in 10-day old embryonated chicken eggs at 35° C. for 3 days. Monovalent 2009 H1N1 pandemic vaccine was obtained from MGH pharmacy. 2009 H1N1 virus was adapted in mice for use in challenge studies after three cycles of intranasal instillation-lung homogenate preparation. The 50% tissue culture infectious dose (TCID50) of live virus was determined in Madin-Darby canine kidney (MDCK, ATCC, #CCL-34) cells. 50% lethal dose (LD50) was determined in young adult and old mice.

Mice were anesthetized by intraperitoneal injection of a mixture of ketamine (80 mg/kg) and xylazine (20 mg/kg) for hair removal, immunization, and challenge. Mice were intradermally injected with 2009 H1N1 pandemic vaccine (0.06 μg HA antigen) by an insulin syringe equipped with a 29G hypodermic needle (ID) alone or with prior NAFP treatment of the target zone (Laser), post topical application of IMIQ, or both (Laser/IMIQ). Imiquimod-treated target zones were covered with a 3M Tegaderm patch to increase the adjuvant effects based on preliminary tests. Mice were challenged by intranasal instillation of 10×LD50 mouse-adapted 2009 H1N1 viruses. Body weight and survival were monitored for 14 days except otherwise specified. Mice with more than 25% body weight drop were euthanized. In some experiments, lung was harvested four days after challenge to measure lung viral titer by TCID50 assay.

The Hemagglutination inhibition (HAI) antibody titers assay was performed following published protocols (Koutsonanos D. G., PLoS One. 2009; 4(3)). Briefly, serum samples were incubated with receptor-destroying enzyme (Denka Seiken, Tokyo, Japan) at 37° C. overnight followed by heat inactivation at 56° C. for 30 minutes. Serum samples were then subjected to a 2-fold serial dilution, incubated with 4 HA units of pandemic viruses at 37° C. for 1 hour, and incubated with 0.5% chicken red blood cells (Charles River Laboratories) at room temperature for 30 minutes. The HAI titer was defined as the reciprocal of the highest dilution that inhibited hemagglutination. Vaccine-specific IgG, IgG1, and IgG2a antibody titers were measured by enzyme-linked immunosorbent assay (ELISA). In brief, influenza vaccine containing 1 μg/ml HA was coated onto the ELISA plate. After incubation with serially diluted serum samples, HRP-conjugated goat anti-mouse IgG, IgG1, or IgG2a antibodies (Invitrogen, CA) were added to detect specific antibody subtypes.

Four weeks later, serum HAI (FIG. 3A), IgG (FIG. 3B), and IgG subtype IgG1 (FIG. 3C) and IgG2a (FIG. 3D) antibody titer were measured. Ratio of IgG2a/IgG1 is shown in FIG. 3E. IgG antibody titer was further measured 12 and 24 weeks after immunization and shown in FIG. 3F.

As shown in FIG. 3A, Laser/IMIQ significantly ($p<0.001$) increased HAI antibody titer as compared to ID immunization alone, or ID in combination with Laser or IMIQ alone. Serum IgG antibody titer showed the same trend as HAI antibody titer (FIG. 3B). Serum IgG1 and IgG2a antibody titer was further measured to evaluate Th1 and Th2 helper T cell immune responses. Laser/IMIQ adjuvant increased pandemic vaccine-induced IgG1 antibody titer and profoundly increased IgG2a antibody titer, which is much more effective in blocking viral infection as compared to IgG1 (FIGS. 3C-D). Comparison of the ratio of IgG2a/IgG1 in adjuvant-incorporated groups with that in the ID immunization alone group indicated that Laser induced a Th2-biased immune response, while IMIQ induced a Th1-biased immune response (FIG. 1E). Interestingly, the combined Laser/IMIQ adjuvant induced a strong Th1-biased immune response as evidenced by a significant increase in the IgG2a/IgG1 ratio in Laser/IMIQ group as compared to IMIQ group (FIG. 3E). The high antibody titer was maintained for at least 6 months (FIG. 3F). In FIG. 3, n=8-10; and *, , * denote $p<0.05$, 0.01, 0.001, respectively.

Due to the importance of cell-mediated immune response in clearance of virus-infected cells and the indication that Laser/IMIQ may induce cellular immunity based on the results above, the stimulation of IFNγ-secreting CD4+ and CD8+ cells in peripheral blood mononuclear cells (PBMCs) 7 days after immunization was measured. One week after mouse immunization as described above, 100-150 μl blood was collected in a heparinized tube by tail vein bleeding. Peripheral blood mononuclear cells were then isolated after red blood cell lysis. Peripheral blood mononuclear cells ($10^6$ cells/ml) were incubated in the presence of influenza vaccine (1 μg/ml HA content) and anti-CD28 antibodies (4 μg/ml) (BD Bioscience Pharmingen, San Diego, Calif.) overnight. Golgi-Plug was then added to prevent cytokine secretion. Five hours later, peripheral blood mononuclear cells were harvested, stained with fluorescence conjugated anti-CD4, -CD8, and -IFNγ antibodies and subjected to flow cytometry analysis. Non-immunized mice were used as control. Percentages of IFNγ-secreting CD4+ T cells and CD8+ T cells in peripheral blood mononuclear cells were significantly increased in Laser/IMIQ group as compared to Laser or IMIQ group (FIG. 4A-B). In FIG. 4, n=8-10; and *, , * correspond to p<0.05, 0.01, 0.001, respectively.

Example 2

Laser/Imiquimod Improves Protection Against Lethal Viral Challenge

BALB/c mice as described in Example 1 were intradermally immunized with pandemic vaccine (0.06 μg HA antigen) alone or in the presence of Laser, Imiquimod, or Laser/Imiquimod adjuvant. Five weeks later, immunized mice as well as non-immunized control mice were intranasally challenged with 10×LD50 of mouse-adapted 2009 H1N1 pandemic virus (0.06 μg HA antigen). Four days later, mice were euthanized and lung was isolated, homogenized and centrifuged.

Figure 3:
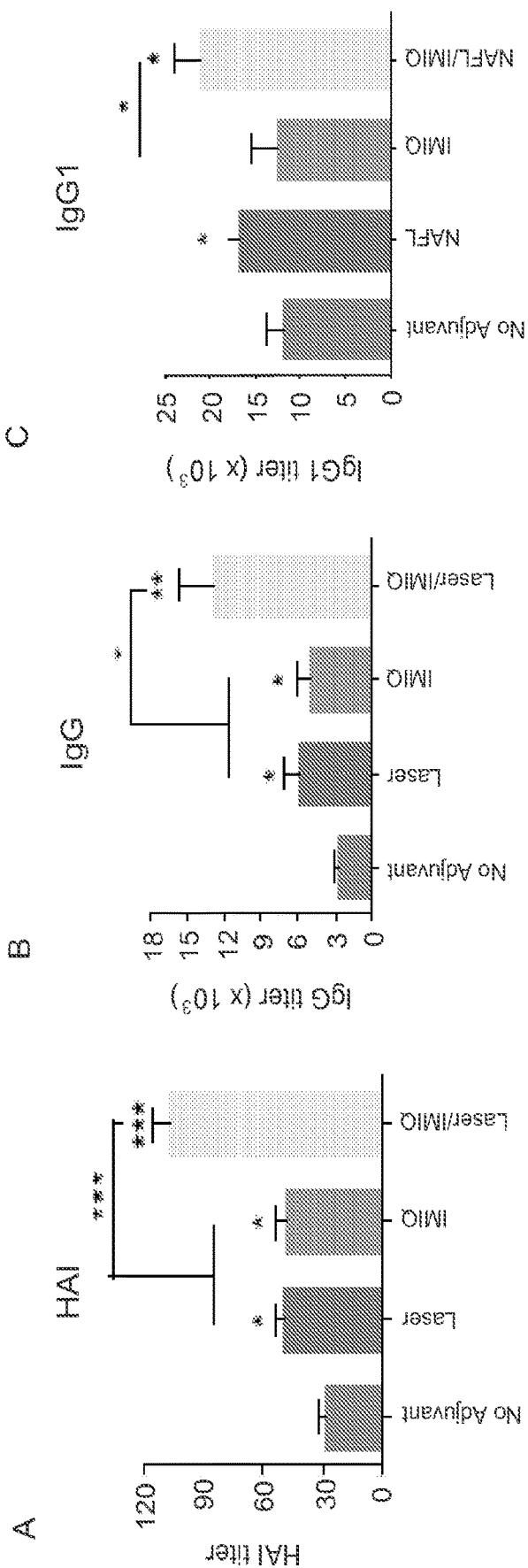
FIGS. 3A-3F are a series of graphs that evidence observed increases in pandemic vaccine-induced humoral immune response following treatment of the target zone with NAFP and/or Imiquimod.
Figure 3A:
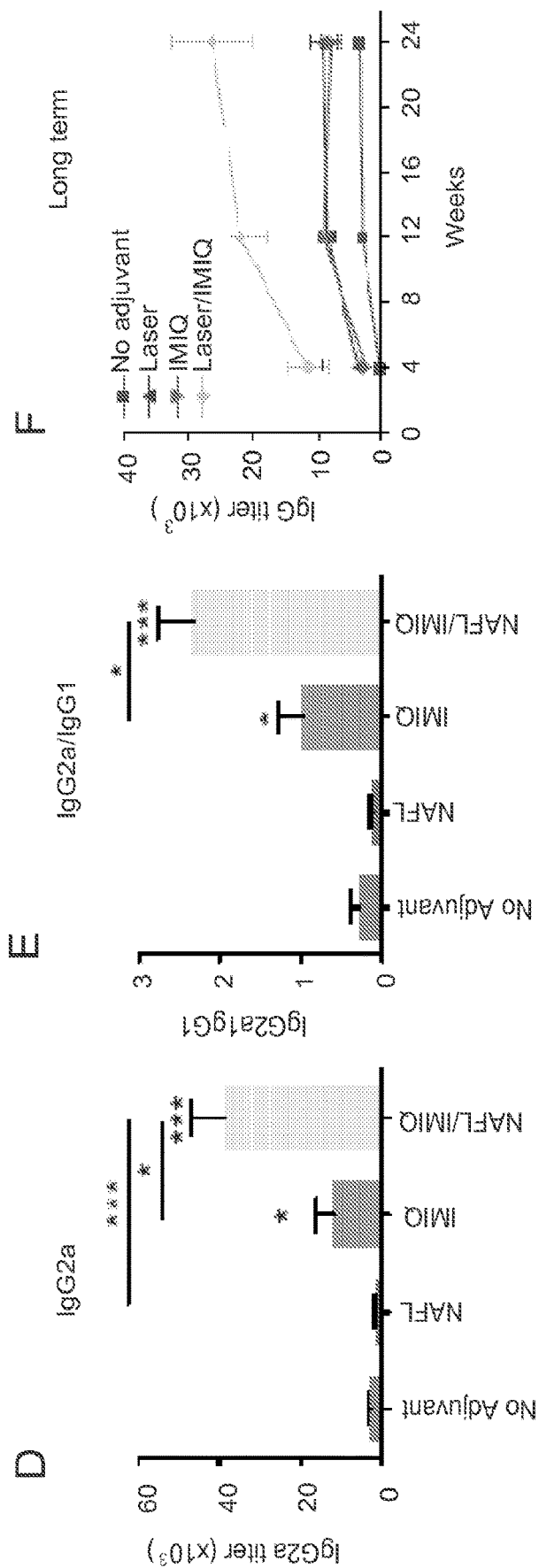

Supernatants were used to infect MDCK cells to determine lung viral titer (FIG. 3A). Five weeks after immunization, Laser/IMIQ treatment reduced lung viral titer to the lowest level at 22 that was ~30 or ~270 times lower, respectively, than those observed with Laser or IMIQ treatment alone (FIG. 5A). Due to the highly pathogenic mouse-adapted pandemic viruses, body weight dropped by more than 10% in all groups (FIG. 5B), with a significantly smaller drop at all times in Laser/IMIQ group (FIG. 5B).

Figure 5:
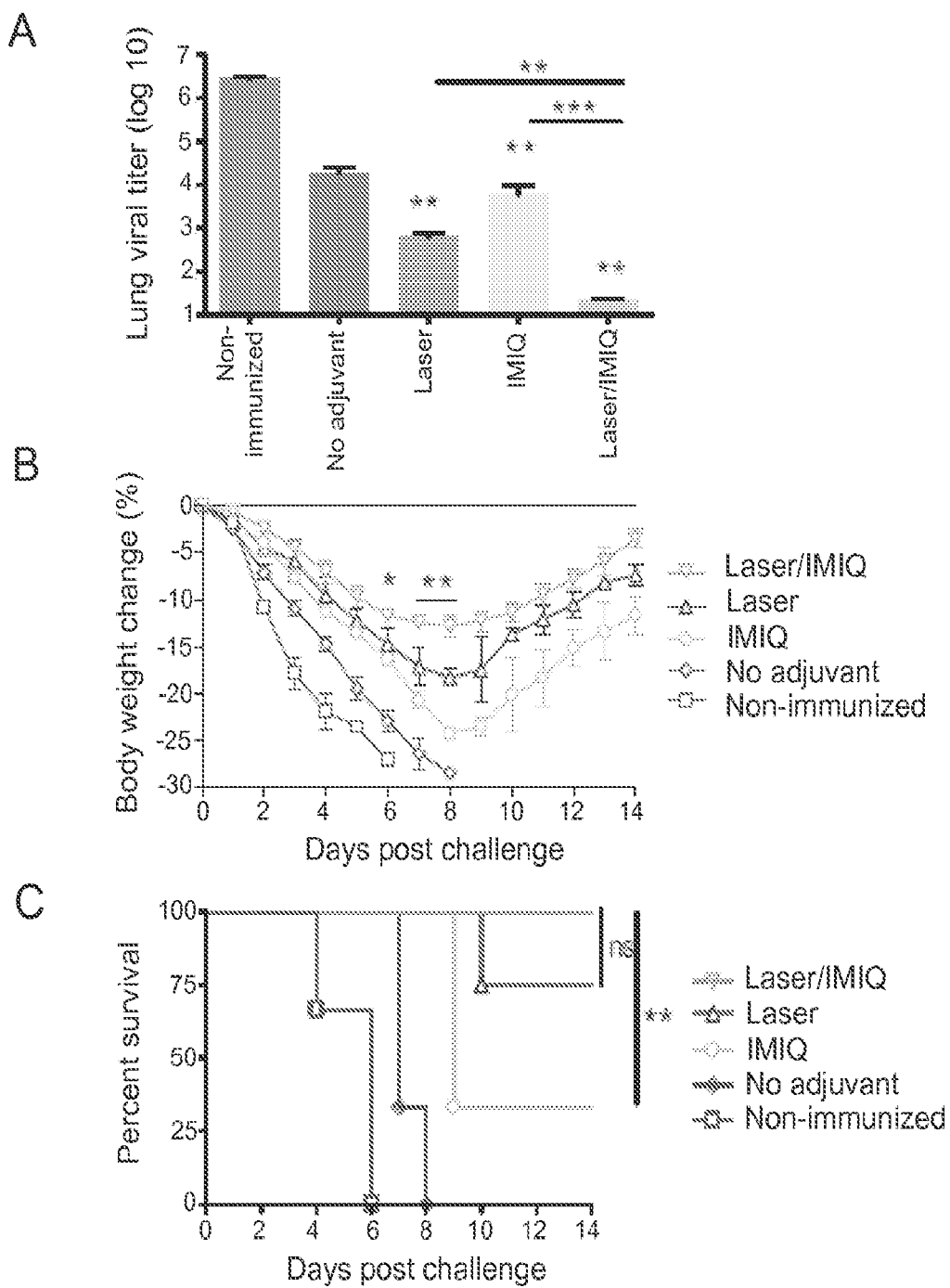
FIGS. 5A-5C are graphs that evidence observed increases in pandemic vaccine-induced protection against a lethal viral challenge following treatment of the target zone with NAFP and/or Imiquimod.

Percent survival (FIG. 3C) was compared between Laser/IMIQ and Laser or IMIQ group by the Logrank test. All mice died within 8 days in non-immunized and no adjuvant group (FIG. 5C), and four out of 6 mice in IMIQ group and 2 out of 8 mice in Laser group died (FIG. 5C). But all mice survived in Laser/IMIQ group (FIG. 5C) and the body weight almost completely recovered at day 14 after challenge and was only 3.5% lower than the body weight at a pre-challenge level (FIG. 5B). The body weight of mice that survived the viral challenge in Laser or IMIQ alone group also recovered similarly 14 days later (FIG. 5B). In FIG. 5, n=8-10; and *, , * correspond to p<0.05, 0.01, 0.001, respectively.

Figure 6:
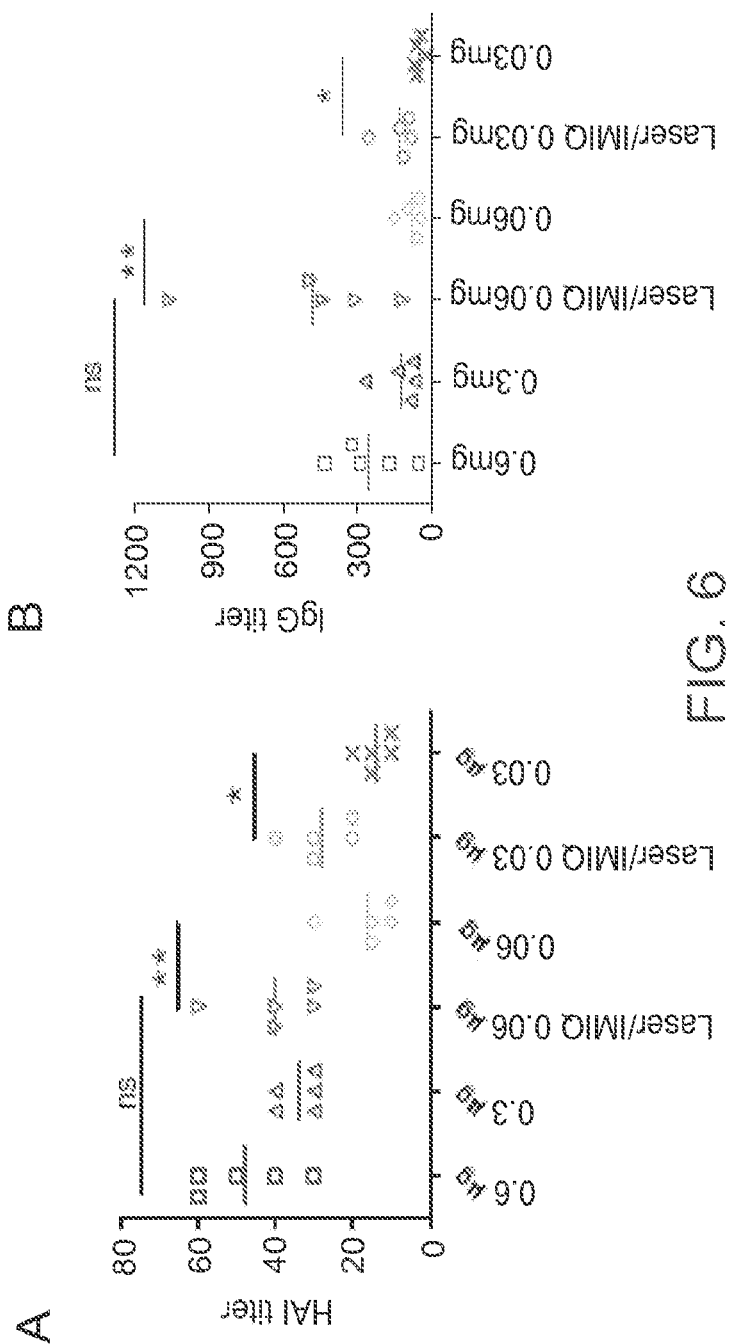
FIGS. 6A and 6B are graphs that evidence dose-sparing effects of Laser/Imiquimod adjuvant. BALB/c mice were ID immunized with pandemic vaccine at high doses (0.6 and 0.3 μg HA antigen) or low doses (0.6 and 0.3 μg HA antigen) in the presence or absence of Laser/Imiquimod adjuvant.

Next, the dose-sparing effects of Laser/IMIQ were evaluated. Mice were intradermally immunized with high doses of pandemic vaccine (0.6 and 0.3 μg HA) without adjuvant or low doses of pandemic vaccine (0.06 and 0.03 μg HA) with or without Laser/IMIQ adjuvant. Four weeks later, serum HAI and IgG titer were measured. As shown in FIG. 6A, the HAI antibody titer in Laser/IMIQ-incorporated 0.06 μg group was comparable to that in 0.3 and 0.6 μg group and the HAI antibody titer in Laser/IMIQ-incorporated 0.03 μg group was comparable to that in 0.3 μg group, but was significantly less than that in 0.6 μg group, indicative of a 5-10-fold dose-sparing with Laser/IMIQ adjuvant. Serum IgG antibody titer shows the same trend as HAI antibody titer (FIG. 6B). In FIG. 6, n=5; and *, ** correspond to p<0.05, 0.01, respectively.

Example 3

Laser/Imiquimod Increases the Number and Maturation of CD11c+Dendritic Cells (DCs) in Draining Lymph Nodes (LNs)

Due to the importance of DCs to prime specific T and B cell responses, total and mature DCs were quantified in draining LNs. BALB/c mice were ID immunized with pandemic vaccine (0.06 μg HA antigen) alone or in the presence of Laser, Imiquimod, or Laser/Imiquimod adjuvant. Six and 18 hours later, draining LNs were harvested and total DCs and CD40- and CD80-expressing DCs were quantified. Single-cell suspensions were prepared, counted, stained with FITC-anti-CD11c (N418), APC-anti-CD40 (3/23) and PerCp-Cy5.5-anti-CD86 (GL-1) antibodies and analyzed by flow cytometry. Total CD11c+ cells and CD40- and CD86-expressed CD11c+ cells per LN were then calculated based on total LN cell number and percentage of each cell subsets.

Figure 7:
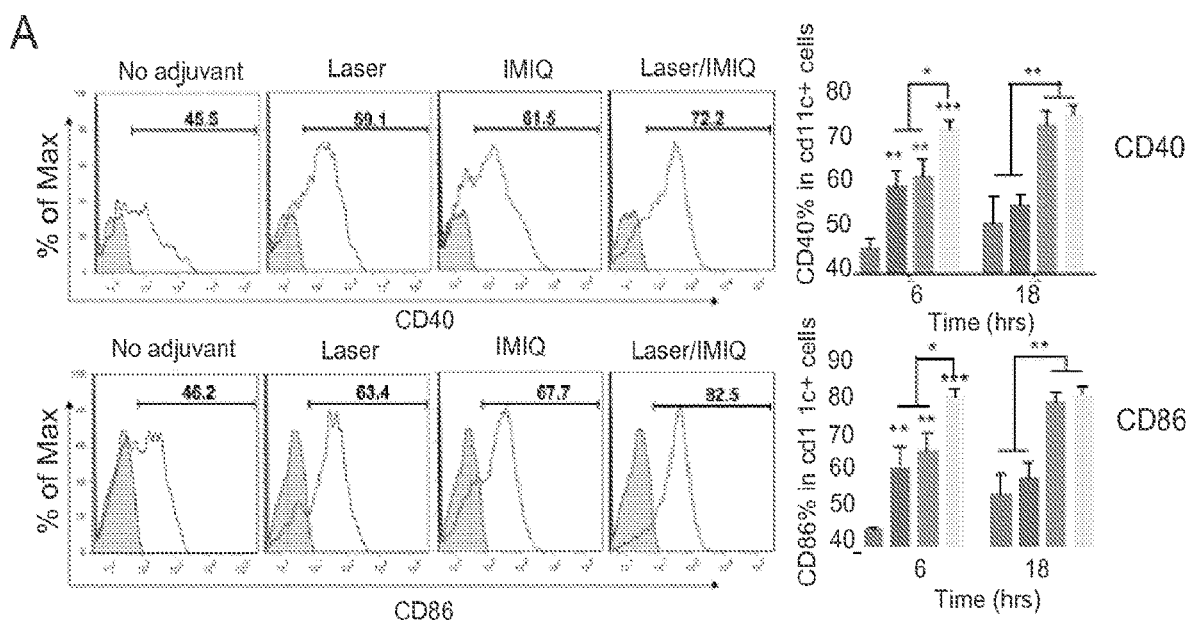
FIGS. 7A-7C are graphs that evidence Laser/Imiquimod increases in total dendritic cells and matured dendritic cells in draining lymph nodes.
Figure 7A:
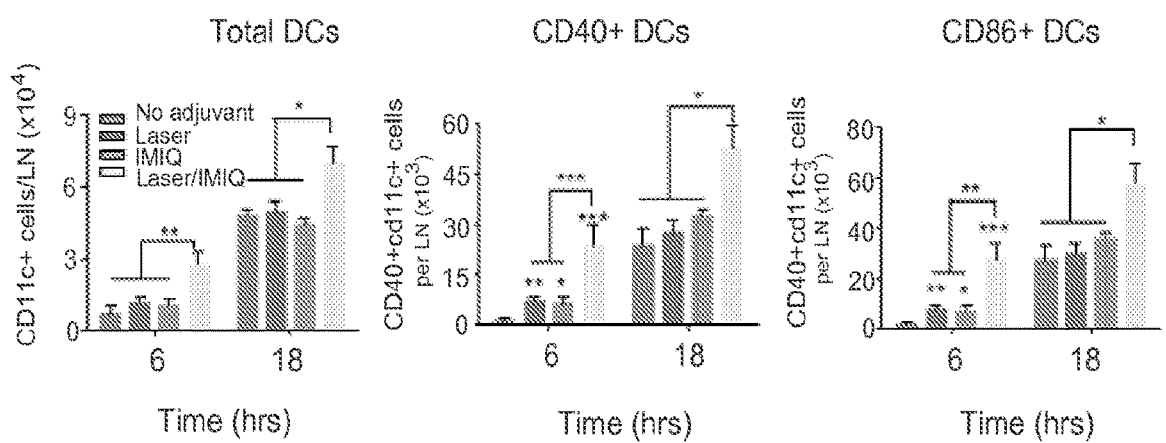
Figure 7B:
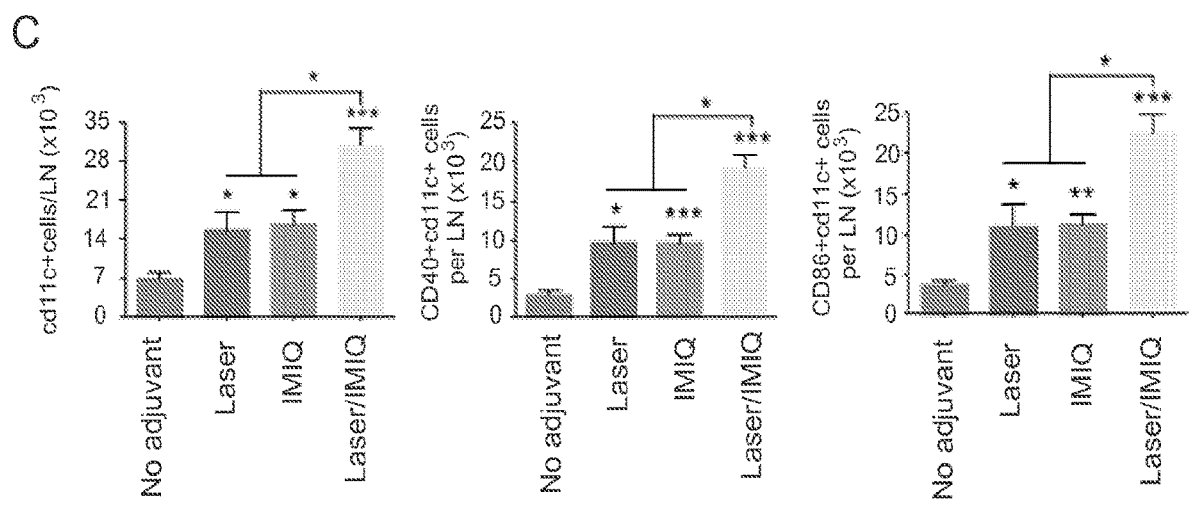

Representative histograms of CD40+ and CD86+DCs 6 hours after immunization are shown in FIG. 7A, where the numbers represent percentages of CD40- and CD86-expressed DCs in total DCs cells. The average percentage of CD40- and CD86-expressed DCs at 6 and 18 hours are shown on the right. As shown in FIG. 7A, Laser/IMIQ significantly increased percentages of CD40- and CD86-expressing DCs in the draining LNs at 6 hours as compared to no adjuvant, or in the presence of either Laser or Imiquimod. Comparable percentages of CD40- and CD86-expressing DCs were found between IMIQ and Laser/IMIQ group at 18 hours, although the percentage of mature DCs in IMIQ or Laser/IMIQ group was still higher than that in no adjuvant or Laser group (FIG. 7A). Laser/IMIQ significantly increased total DCs and CD40- and CD86-expressing DCs at both 6 and 18 hours as compared to no adjuvant, Laser, or Imiquimod group (FIG. 7B). Total CD40- and CD86-expressing DCs were also significantly higher in Laser or Imiquimod group as compared to the no adjuvant group at 6 hours but not 18 hours (FIG. 7B). These results indicate that more DCs with a mature state can be induced by incorporation of Laser/IMIQ adjuvant in ID pandemic vaccine immunization. The increased number of total and mature DCs could also be induced by Laser/IMIQ adjuvant in the absence of pandemic vaccine immunization. As shown in FIG. 7C, more DCs and matured DCs were found in Laser/IMIQ group as compared to Laser or IMIQ group in the draining LNs 18 hours after adjuvant treatment. The significant increases in the number of CD40- and CD86-expressing DCs in the draining LNs are consistent with a significantly higher level of humoral and cellular immune responses against flu vaccine as observed in the previous examples (FIGS. 3-4).

Example 4

Immune-Enhancing Effects of Laser/Imiquimod in Old Mice

Elderly populations often have a low response rate to seasonal or pandemic vaccine immunization due to age-induced immunosenescence. To find whether Laser/IMIQ adjuvant can enhance pandemic vaccine-induced immune response in the elderly, BALB/c mice (18 months old) were ID immunized with 0.6 µg pandemic vaccine without adjuvant or in the presence of Laser, IMIQ, or Laser/IMIQ adjuvant. Intramuscular (IM) immunization of old and young adult mice was used as controls. Four weeks later, serum HAI and IgG antibody titer were measured. Laser/IMIQ adjuvant significantly increased HAI antibody titer at levels comparable to or higher than IM immunization of the same antigen dose in young adult mice. No significant HAI antibody production in old mice IM immunized with the same amount of antigen was observed (FIG. 8A). These results strongly suggest that Laser/IMIQ adjuvant is able to overcome age-related immunosenescence to significantly enhance pandemic vaccine-induced immune response.

Figure 8:
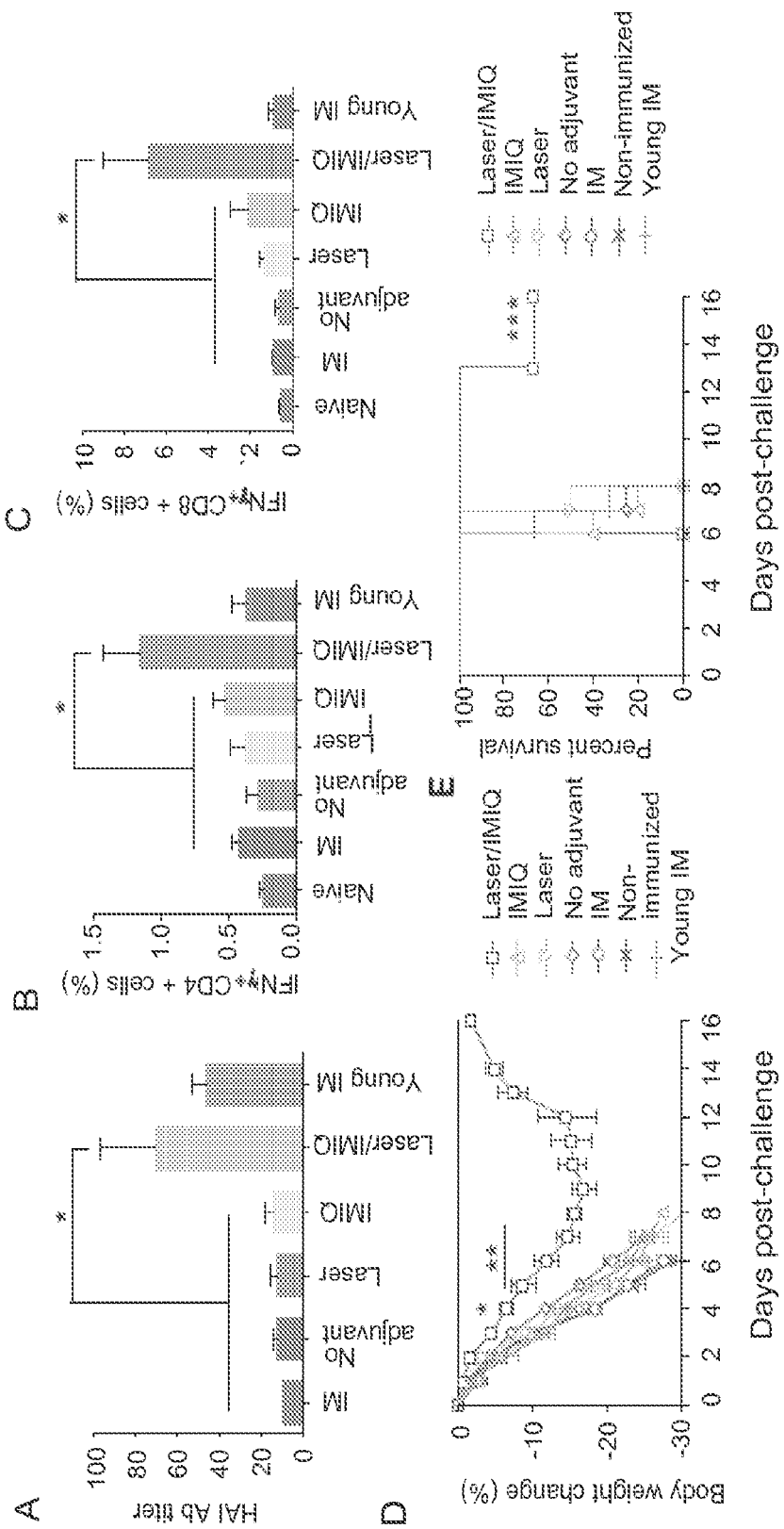
FIGS. 8A-8E are graphs that evidence Laser/Imiquimod improvement of pandemic vaccine immunogenicity in old mice.

Given the importance of cell mediated immunity in immune protection against flu infection in the elderly, cell-mediated immune response was also evaluated. To measure cellular immune response, percentage of IFNγ-secreting CD4+ and CD8+ T cells was analyzed as in young adult mice, 1 week after immunization. In comparison with Laser or IMIQ alone, the percentages of both IFNγ-secreting CD4+ T cells and IFNγ-secreting CD8+ T cells were increased significantly in Laser/IMIQ group as compared to controls (FIG. 8B-C). Five weeks after immunization, mice were challenged with 5×LD50 of mouse-adapted 2009 H1N1 viruses. Body weight and survival were monitored for 16 days after challenge. The body weight drop exceeded 25% within 7 days after challenge in all groups except for Laser/IMIQ group (FIG. 8D). The body weight drop was significantly alleviated in Laser/IMIQ group as compared to Laser or IMIQ alone group and almost completely recovered within 16 days (FIG. 8D). All mice in other groups died or were euthanized due to >25% body weight drop within 8 days, while 4 out of 6 mice survived the lethal viral challenge in Laser/IMIQ group (FIG. 8E, p<0.001). In FIG. 8, n=6-8; and *, , * represent p<0.05, 0.01, 0.001, respectively.

Example 5

Adjuvant Effects of Laser/Imiquimod in Pigs

The potency of Laser/IMIQ adjuvant to enhance pandemic vaccine-induced immune response was further explored in larger mammals having skin properties similar to humans. Yorkshire pigs (~4 months old) were obtained from Tufts University. Hair on the exterior hind leg skin of Yorkshire pigs was shaved. A 1 ml syringe equipped with a 26G hypodermic needle was used to inject 100 µl 2009 pandemic vaccine 2009 H1N1 vaccine (3 µg HA antigen) into the exterior hind leg skin alone or in the presence of Laser, Imiquimod, or Laser/Imiquimod adjuvant. Pigs were anesthetized by intramuscular injection of telazol (2.2 mg/kg)/xylazine (2.2 mg/kg)/Atropine (0.04 mg/kg) and maintained under inhalation isoflurane (2-3%) during hair removal and immunization.

Because the MTZs induced by the laser were limited within a depth of 200 µm from the skin surface, which was mainly within the epidermal tissue of the pig skin, a different clinical laser (Fraxel SR-1500) was used to generate MTZs to reach the dermal tissue of the pig skin. No significant difference was found in HAI antibody titer (FIG. 9A) or IgG antibody titer (FIG. 9B) before immunization among the different groups. Incorporation of Laser/Imiquimod into ID immunization increased HAI antibody titer by 5.3 times and IgG antibody titer by 11.1 times (FIGS. 9A-B), while incorporation of Laser alone only increased HAI antibody titer by ~2.0 times and IgG antibody titer by ~2.5 times (FIGS. 9A-B), which is similar to the immune enhancement observed in BALB/c mice (FIGS. 3A-B).

Whether a combination of the laser illumination, ID Flu vaccine, and Imiquimod caused any undesirable side effects was examined. No significant alteration in the skin appearance in mice was observed. As can be seen in FIG. 9C, flu vaccine caused significant erythema and swelling at the injection site in pigs, which peaked in day 3 and completely resolved in day 7 post-immunization, similar to what has been described in humans. Similar skin responses were seen at the injection site immediately (day 0, <30 min) and day 1 after immunization into laser-treated site, but the skin responses were diminished in day 3. Diminished skin irritation was also observed in days 1 and 3 in the presence of Imiquimod or Laser/Imiquimod adjuvant, in sharp contrast to the peaked skin irritation occurring in the ID group during the same period of time. The improved safety profile may be ascribed to acceleration in migration of DCs from the skin to the draining LNs and/or reduced production of IL-1β. Therefore, Laser/IMIQ did not worsen, but rather reduced the adverse effects of ID flu vaccine in swine.

Example 6

Non-Ablative Fractional Photothermolysis (NAFP) Induces the Production of Pro-Inflammatory Cytokines NAFP generates an array of MTZs that are micro-columns of thermally denatured skin with controlled width and depth, leaving up to 95% of the skin uninvolved. The healthy surrounding tissue allows fast epidermal repair via migration of the surrounding viable cells. The laser does not produce any holes in the skin as stratum corneum remains "intact," protecting bacteria from entering the skin. However, the permeability of the MTZs to molecules may be increased, allowing better penetration of topically applied Imiquimod to the dermis and interaction with antigen-presenting cells around each MTZs (FIG. 11A).

Figure 9:
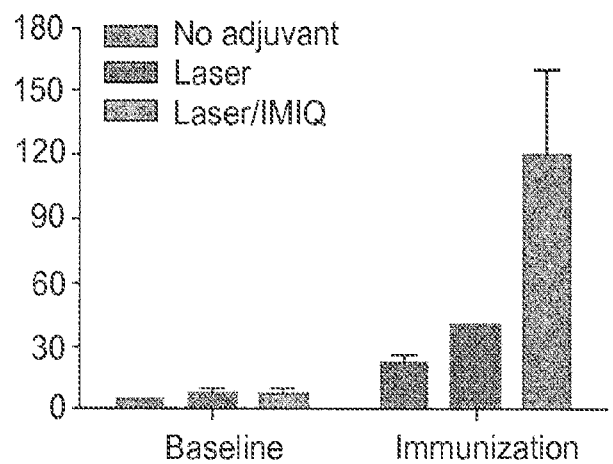
FIGS. 9A and 9B are graphs and FIG. 9C provides a series of images that evidence Laser/Imiquimod improvement in pandemic vaccine-induced immune response in pigs.
Figure 9:
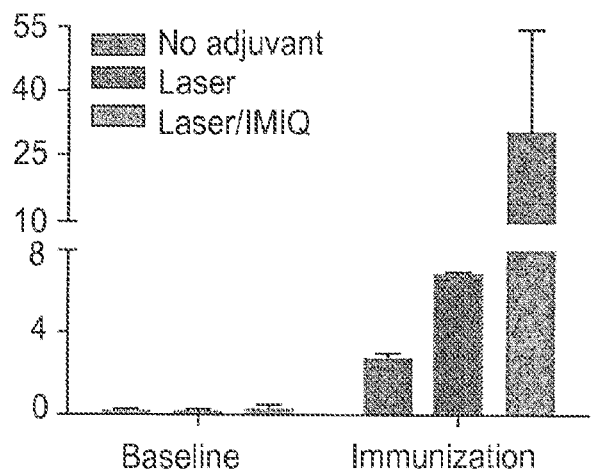
Figure 9A:
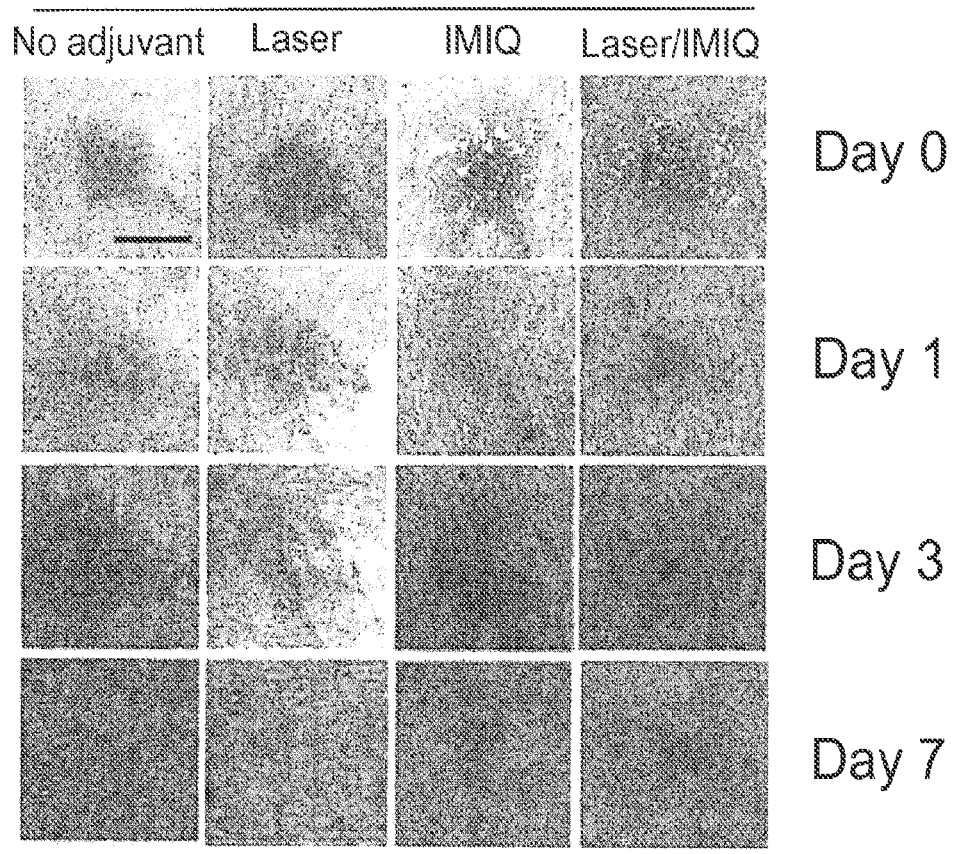
Figure 10:
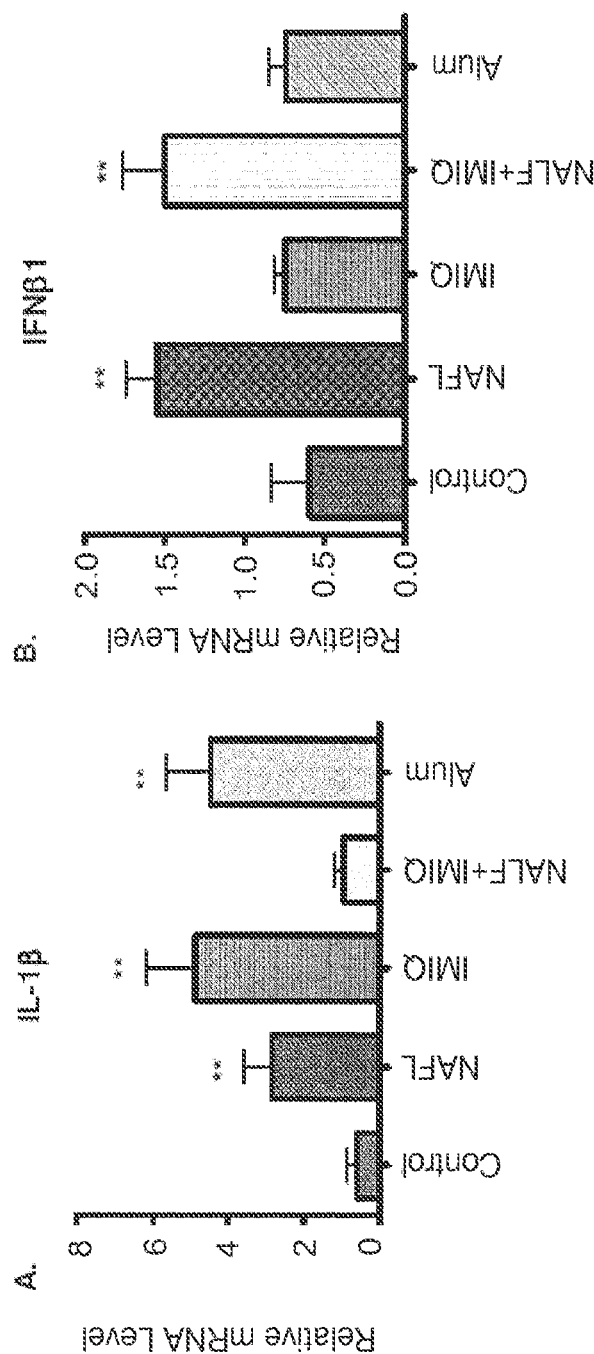
FIGS. 10A and 10B are graphs that evidence production of inflammatory cytokines in the skin following treatment with laser, Imiquimod or Laser/Imiquimod.

These injured cells in MTZs can release "danger signals" that are recognized by the immune system to elicit inflammation aimed at clearance of the injured cells as the first step of a normal healing process, also called sterile inflammation. Such host-derived non-microbial stimuli released following tissue injury or cell death can activate the host immune system to induce sterile inflammation that either resolves the injury or leads to autoimmune disease. The "danger signals" released from the dead cells may include double strand (Ds) DNA, ATP, RNA, uric acid, hyaluronan, and so on. The "danger signals" can be sensed by Toll-like receptors (TLRs) on antigen presenting cells (APCs), which activates inflammasomes resulting in production of ILL IL-12, IFNβ1, etc. Indeed, non-ablative fractional laser (NAFL) significantly induced the production of these pro-inflammatory cytokines at the skin in the absence of antigen (FIG. 10A). Therefore, the "danger signals" released from NAFL-injured cells function as vaccine adjuvants. While IFN β1 is absolutely essential for virus-induced immunity, IL-1β can cause unwanted skin inflammation. Therefore, Imiquimod was topically applied to the skin after vaccination, resulting in a high level of IFN1β but a low level of IL-1β (FIG. 10B). Without wanting to be bound by theory, a high level of IFN1β but a low level of IL-1β may be the underlying mechanism for boosting flu-induced immunity but reducing skin irritation (FIG. 9).

Figure 11:
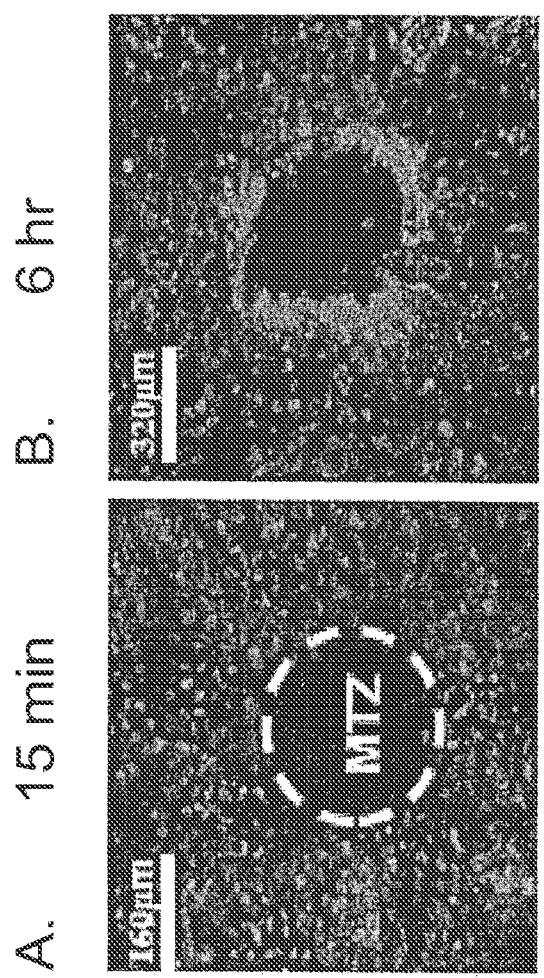
FIGS. 11A-11D are graphs that evidence observed altered distributions of antigen-presenting cells (APCs) around MTZs and an increase in the number of mature dendritic cells in draining lymph nodes by laser-Imiquimod treatment.
Figure 11A:
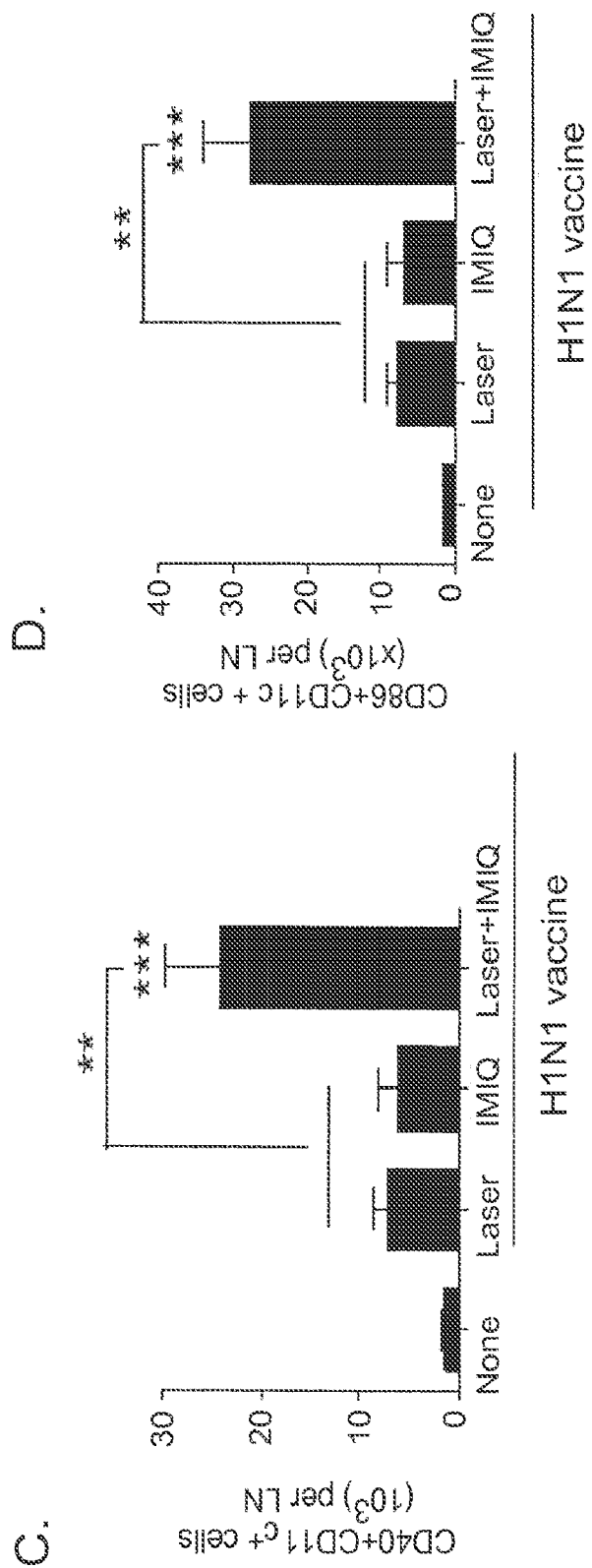

FIG. 11 depicts altered distribution of APCs around and permeability of MTZs and an increase in the number of mature DCs in the dLNs by Laser-IMIQ treatment. MHC II-EGFP transgenic mice that express a MHC II molecule infused with enhanced green fluorescent protein (MHC II-EGFP) were used in the intravital confocal imaging study. The low dorsal skin of the mice was treated by ImBooster, and imaged for MHC II+ cells in 15 minutes or 6 hours (FIGS. 11A-B). Alternatively, the ears of the mice were treated with the device followed by topical application of a patch containing red fluorescently labeled OVA (FIGS. 11C-D). One representative result of four separate experiments performed. The cells from the dLNs were isolated 6 hours after 0.5 μg HA of 2009 H1N1 flu vaccine was ID administered into sham-treated mice (none) or laser-treated site with or without subsequent Imiquimod application. The isolated cells were stained with anti-CD11c and anti-CD40 or CD86 Ab and analyzed by flow cytometry.

Antigen-presenting cell distribution following laser illumination in MHC II-EGFP mice was tracked by intravital confocal scanning microscopy. MHC-II molecule is expressed in antigen-presenting cells that include macrophages, dendritic cells, and B cells. As can be seen in FIG. 11A, laser NAFP illumination killed cells in the MTZs, as shown by the lack of GFP expression in the cells, but the cells surrounding these MTZs were viable, as shown by the expression of GFP (FIG. 11B). These GFP-expressing cells are mainly macrophages, Langerhans cells and DCs, broadly defined as antigen-presenting cells. Antigen-presenting cells migrated toward the MTZs, and accumulated in a large number around each MTZ over a 6 hour period (FIG. 11B). Imiquimod topically applied to the laser-treated site penetrates into the skin through the MTZs, interacts with antigen-presenting cells in the vicinity of the MTZs, and induces their maturation at a high efficiency. In accordance with activation of antigen-presenting cells by NAFL, a higher number of CD11c+ cells expressing CD40 or CD86 costimulatory molecule were detected in the dLNs 6 hours after mice were ID immunized with 2009 H1N1 flu vaccine adjuvantated by laser-Imiquimod, compared to control mice receiving vaccine alone, vaccine-IMIQ or vaccine-laser (FIG. 11C-D). The high number of mature DCs in the dLNs was accompanied by their reduction in the site of vaccine injection (data not shown), suggesting accelerated migration of mature DCs from the skin to the draining lymph nodes.

Example 7

NAFL/IMIQ Topical Adjuvant Boosts Flu Vaccine

Results

Figure 12:
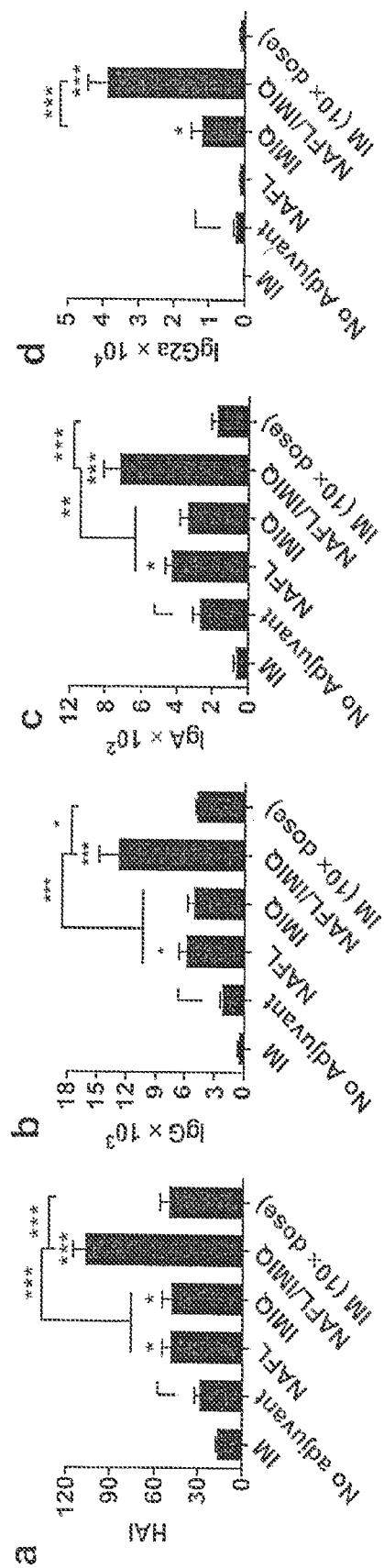
FIGS. 12A-12G are graphs that evidence Non ablative fractional laser/Imiquimod (NAFL/IMIQ) strengthens immunogenicity of ID flu vaccine.
Figure 12A:
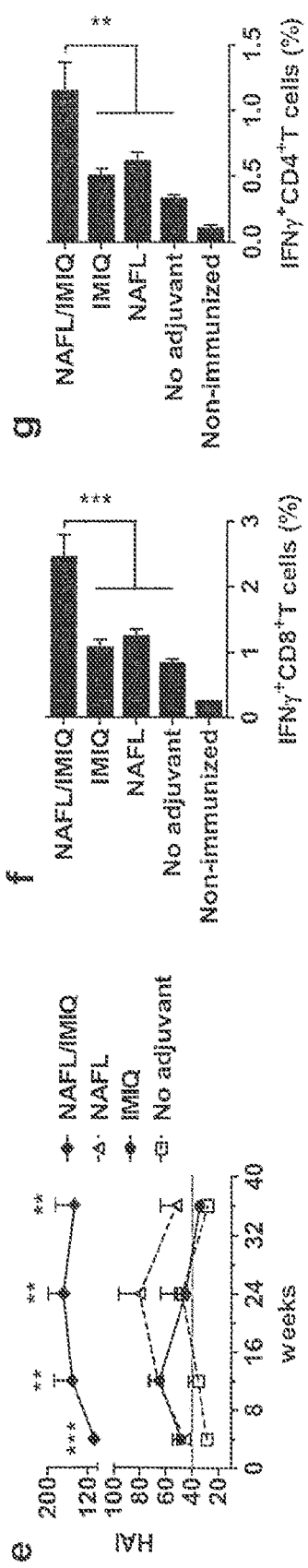
Figure 12B:
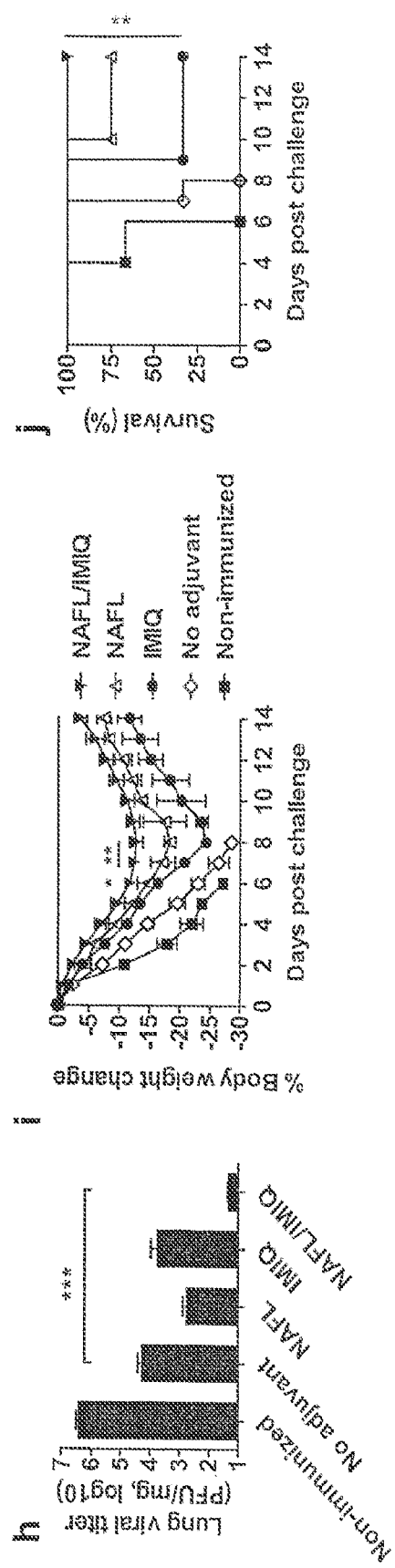

The over-the-counter, handheld, cosmetic NAFL generated a 6×9 array of MTZs in a 7×10 mm² area of the skin. Each MTZ was similar in size as a hair, about 200 μm in diameter and 300 μm in depth and healed quickly, giving rise to new and younger skin. The sterile inflammation induced by laser-damage cells was restricted around each MTZ, leaving a majority of tissues unaffected, which ensured quick resolution of the sterile inflammation. To test whether this short life sterile inflammation could augment vaccination, a clinic H1N1 flu vaccine (A/California/7/2009) was ID inoculated into the site of laser illumination. After 4 weeks, hemagglutinin inhibition (HAI) antibody titers were found to be significantly higher in the presence of laser pre-treatment than in the absence of the treatment (FIG. 12a, $p<0.05$, ANOVA/Bonferroni). In parallel studies, ID inoculation was slightly greater than IM injection of the same amount of the vaccine (FIG. 12a), similar to previous investigations. Comparable results were also attained with protein model antigen ovalbumin (OVA), Hepatitis B surface antigen vaccine (HBsAg) or recombinant flu HA protein (rHA), raising specific antibody titers by 6- ($p<0.001$, t-test), 10- ($p<0.05$, t-test) and 3- ($p<0.01$, t-test) folds, respectively, in the presence vs. absence of laser pre-treatment. We subsequently focused our investigation on licensed flu vaccines and corroborated whether the adjuvant effect of NAFL was primarily ascribed to laser-mediated cell damage by co-injection of flu vaccine with heat-damaged skin cells. When flu vaccine was mixed with a small number of heat (65° C. or 95° C.)-damaged skin cells and ID administered, the heat-damaged cells enhanced immune responses against the co-injected flu vaccine at a level comparable to that of laser treatment, significantly higher than the flu vaccine alone ($p<0.01$ for 65° C. and $p<0.05$ for 95° C., ANOVA/Bonferroni). The laser adjuvant conferred similar adjuvant effects as that of the topic IMIQ cream (Aldara, 3M Pharmaceuticals) which is a FDA approved topical drug for treatment of some skin disease (see FIG. 12a). Strikingly, when laser-treated skin was inoculated with the flu vaccine, followed by topical application of the IMIQ cream, the combination synergistically enhanced HAI titers by 7-folds or 4-folds over IM or ID vaccination, respectively (see FIG. 12a, $p<0.001$, ANOVA/Bonferroni). This robust response could not be recapitulated by IM immunization of a 10×higher amount of the vaccine, suggesting at least 10×dose-sparing over the current IM flu vaccination (see FIG. 12a). Similar trends were attained in total serum IgG and IgA levels (FIG. 12 b, c). The adjuvant effect was also confirmed in outbred Swiss Webster mice in which IgG and HAI titers were robustly higher with laser pre-illumination than without it. We also confirmed that IMIQ, not the vehicle cream, conferred the synergistic adjuvant effect because no such effect was observed when flu vaccine was given, along with NAFL and vehicle cream, in spite of recent report showing that the vehicle cream of Aldara could stimulate innate immunity.

In humans, a majority of people are primed with influenza viral antigens either via vaccination or natural infection. To test if the adjuvant could boost the immune response efficiently in antigen-primed subjects, mice were primed with H1N1 influenza vaccine with or without NAFL or NAFL/IMIQ, followed by a booster immunization two weeks later. The adjuvant was found to boost immune responses in primed subjects as effectively as in naïve ones, regardless of whether or not the primary vaccination was given flu vaccine alone or the vaccine in combination with NAFL or NAFL/IMIQ adjuvant.

Measurement of serum IgG1 and IgG2a antibody titers revealed Th1-skewed immune responses evoked by the NAFL/IMIQ adjuvant. It profoundly elevated IgG2a production by 15-folds whereas only a 5-fold increase was seen with IMIQ or none with NAFL (FIG. 12d, $p<0.001$, ANOVA/Bonferroni). NAFL stimulated mainly IgG1 production, indicative of Th2 immune responses. A combination of IMIQ with NAFL also increased IgG1 antibody production, but the extent of such an increase was much less pronounced, giving rise to a greater ratio of IgG2a to IgG1. The results argue strongly that application of IMIQ on the NAFL-treated site is not a simple combination of Th2 and Th1 responses, rather resulting in a stronger Th1 immune response that is more effective in protection against viral infection.

The superior humoral immune response was sustained at a ~1:160 HAI titer for at least 9 months without any sign of decline (FIG. 12e), a period of time longer than a flu season which typically lasts for 6 months in the most parts of the world. NAFL alone was also able to retain a HAI titer above the standard protective level (1:40) for more than 9 months (FIG. 12e). In comparison, topical IMIQ was not as strong as NAFL in sustaining HAI production, and the HAI titer in the animals started to decline after 3 months to levels similar as non-adjuvanted flu vaccine (FIG. 12e). The IgG level in NAFL/IMIQ group was substantially higher than all other groups throughout the entire experimental period. Not only humoral but cellular immune responses were also affected by NAFL/IMIQ adjuvant. The percentages of IFNγ-secreting CD8+ and CD4+ T cells in the periphery in response to flu viral stimulation were vigorously increased only in NAFL/IMIQ group among all groups tested (FIG. 12f, g, $p<0.001$ or 0.01 ANOVA/Dunnett's).

Protection Against Viral Infection

The immunized mice were challenged with a mouse-adapted A/California/7/2009 H1N1 virus. The NAFL/IMIQ adjuvant greatly reduced lung viral titer to $2.2 \times 10^1$ PFU/mg tissue ($p<0.001$, ANOVA/Bonferroni) which was 1,000 times lower than that attained in mice receiving the vaccine alone (FIG. 12h). Moreover, while the body weight dropped by more than 17% in all other groups in 8 days post-infection, the body weight in NAFL/IMIQ group declined at a slowest pace and subsequently recovered at a fastest pace (FIG. 12i). All mice died within 8 days in non-immunized group or mice immunized similarly without any adjuvant (FIG. 12j). Four out of 6 mice died in IMIQ group and 2 out of 8 mice died in NAFL group, whereas no mice died (0/8) in NAFL/IMIQ group (FIG. 12j). The highest survival rate of NAFL/IMIQ group was in a good agreement with the lowest morbidity in these mice as shown by a body weight change. Similar results were also obtained in Swiss Webster mice as suggested by substantial reduction of flu viral replication in the lung of animals immunized with flu vaccine in the presence of the NAFL/IMIQ adjuvant as compared to the vaccine alone.

A Favorable Safety Profile Compared to Squalene Based Adjuvant

A safety profile of the adjuvant was compared with that of AddaVax (Invivogen), which has a similar formulation and physical/chemical features as MF59 used in licensed flu vaccines in Europe. IM injection of flu vaccine emulsified with an equal amount of AddaVax provoked immune responses slightly inferior to that of the NAFL/IMIQ adjuvant, as measured by IgG and HAI titers (FIG. 13a, b), suggesting that the laser-based adjuvant is at least equal to or better than the squalene-based adjuvant in augmentation of flu vaccines. While greatly enhancing flu vaccines, NAFL/IMIQ caused no overt skin lesion at the inoculation site, although mild inflammation was noticed in one day and disappeared within 3 days with histological examination (FIG. 13c right panel). Similar to a previous investigation, coagulate columns were generated in dermis by the laser, with intact stratum corneum and epidermis in place, by which skin infection can be prevented and safety be warranted (FIG. 13c right panel). In contrast, IM administration of AddaVax mixed with flu vaccine caused severe inflammation that persisted for more than one week (FIG. 13c left panel). Moreover, compared with AddaVax, NAFL/IMIQ induced a much lower level of pro-inflammatory cytokine responses systemically as manifested by a relatively lower level of blood IL-6 or TNF-α, important mediators of fever (FIG. 13d, and data not shown). IL-6 concentration peaked after 8 hours of immunization and reached as high as 134 pg/ml in mice receiving squalene-adjuvanted flu vaccine, which was 4 times higher than the 32 pg/ml IL-6 in mice immunized by the same amount of vaccines with the NAFL/IMIQ adjuvant (FIG. 13d, $p<0.01$ t-test). Neither adjuvant affected the body weight (data not shown), but squalene-adjuvanted vaccine elevated the body temperature by 1° C. when compared with mice receiving the vaccine alone (FIG. 13e). The high temperature lasted for 9 hours, in agreement with clinical studies showing a high rate of fever in patients receiving adjuvanted (MF59 or AS03) flu vaccines. In sharp contrast, no fever was measurable over the vaccine alone in NAFL/IMIQ group (FIG. 13e). To the best of our knowledge, the adjuvant represents the first one that can augment immune responses at little cost of safety locally and systemically, in marked contrast to squalene-based adjuvant.

Safety and Effectiveness in Swine

Figures 2A, 2B:
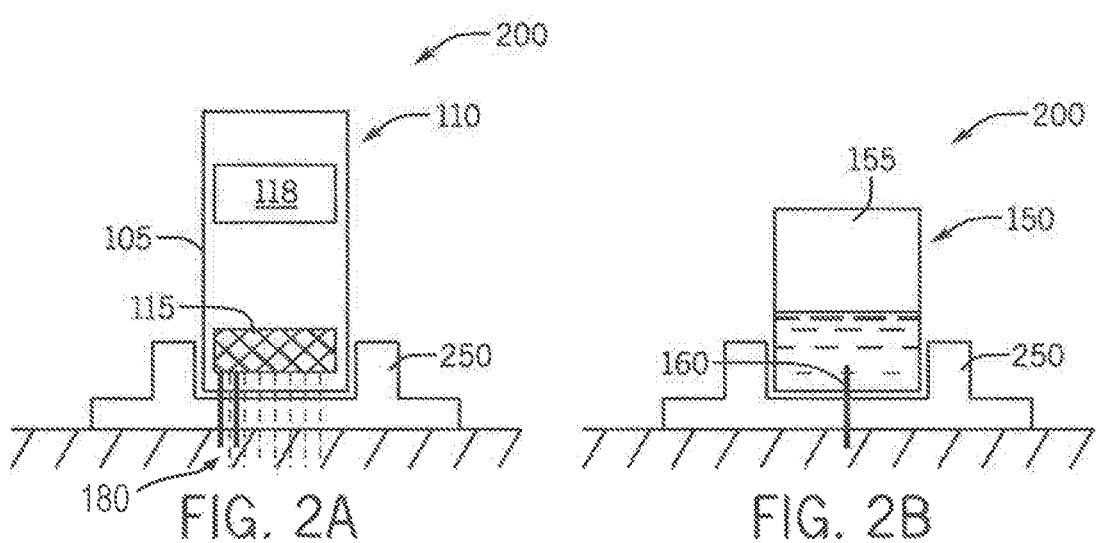
FIGS. 2A and 2B are schematic illustrations of an exemplary system in accordance with further exemplary embodiments of the present disclosure.
Figure 14:
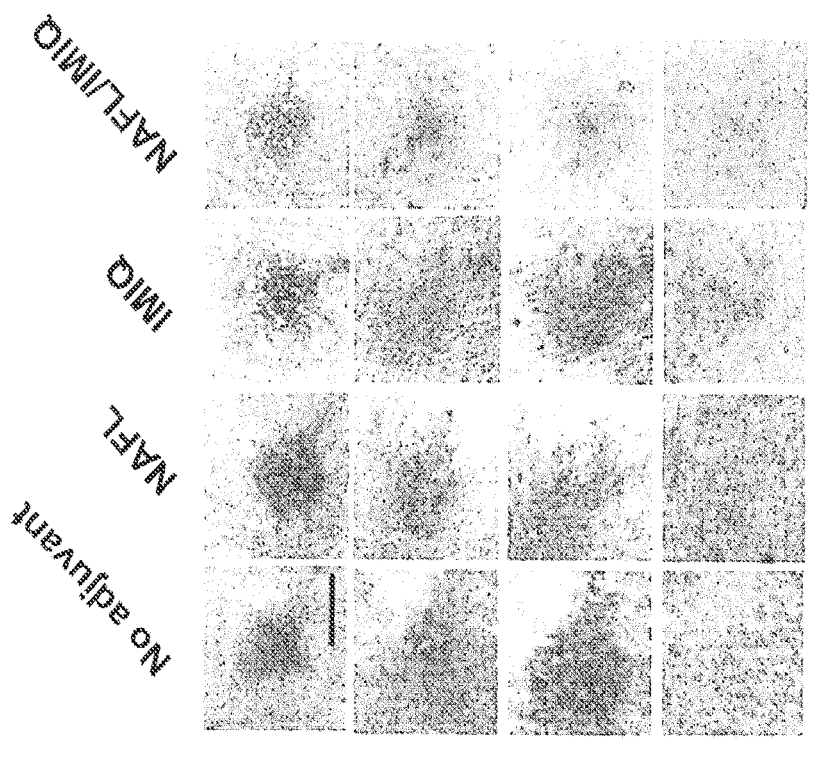
FIGS. 14A-14G are graphs from a NAFL/IMIQ adjuvant in swine study.
Figure 14:
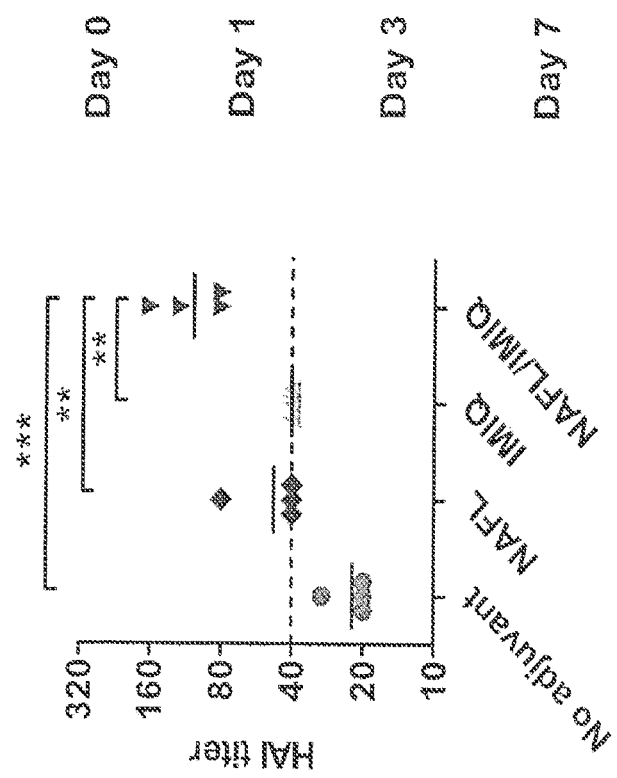
Figure 14A:
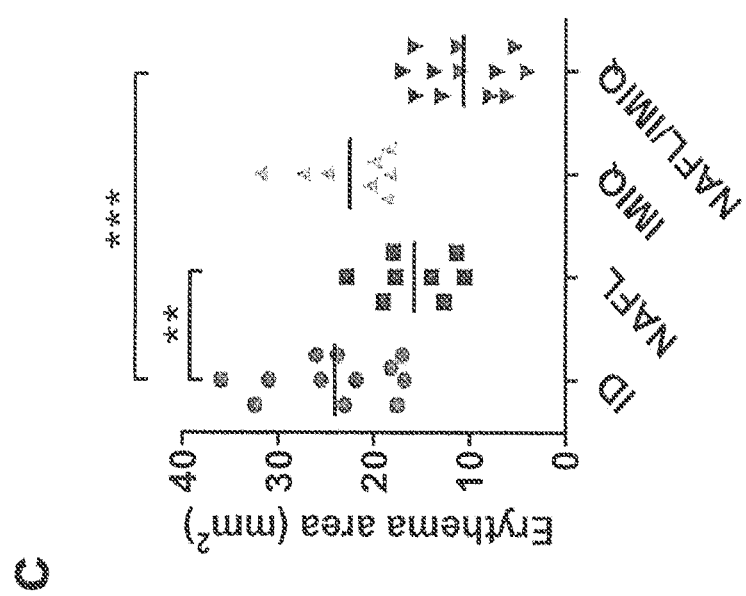
Figure 14B:
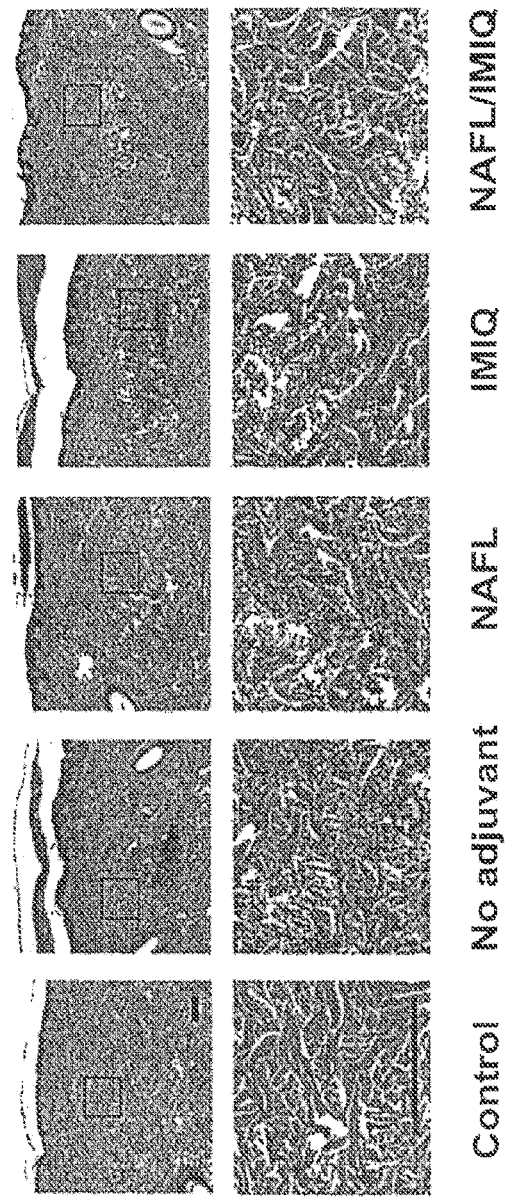

Its safety and potency was further evaluated in swine because porcine skin resembles human skin in term of anatomy, immune responses, and pharmacokinetics. Because of a thicker skin of pigs than mice, we used another cosmetic, non-ablative fractional laser, named Fraxel SR-1500 (Solta Medical) for pig studies. This clinical device emitted a laser with 17% coverage, 93 MTZs/cm$^2$/pass and 35 mJ/microbeam. After one pass of the laser treatment, the pigs were ID vaccinated with 3 μg HA of 2009 H1N1 vaccine, equivalent to a full dose of ID Flu vaccine in humans in the basis of body weight. The immunization enhanced HAI titers by ~2-fold compared to ID vaccine alone (FIG. 14a). The laser treatment also increased the production of HBsAg-specific Ab by more than 5~7-folds in both primary and boosting immunizations. Addition of topical IMIQ further enhanced the immunogenicity in pigs similarly as described in the mouse study (FIG. 14a), but remarkably, concurred with diminished local skin reactogenicity. As can be seen in FIG. 14b, 1$^{st}$ column, ID flu vaccine caused wheals with a diameter of 0.5-1 cm right after immunization, concurrent with significant erythema and swelling at the injection site, which peaked in day 3 and resolved in day 7 post-immunization, similar to what has been described in humans. Similar or less skin response was observed at the injection site immediately (day 0, <30 min) or day 1 after immunization into laser-treated site, however it diminished considerably with laser pre-treatment in day 3 compared to flu vaccine alone (FIG. 14b 2$^{nd}$ column). Diminished skin irritation was further appreciated in days 1 and 3 by combination of NAFL and IMIQ (FIG. 14b 4$^{th}$ column), in sharp contrast to the peaking skin irritation in ID group during the same period of time (FIG. 14b 1$^{th}$ column). The milder skin reactogenicity was clearly suggested by 50% reduction in the mean area of erythema at the inoculation site in the NAFL/IMIQ group as compared to flu vaccine alone when multiple inoculation sites were analyzed at day 3 by Image Pro Premier program (FIG. 14c, 11 vs. 23 mm$^2$, $p<0.001$, ANOVA/Bonferroni). In parallel, histology examination of the inoculation sites confirmed drastic diminishment of infiltrated inflammatory cells in pigs receiving flu vaccine adjuvanted by NAFL/IMIQ as compared to the pigs receiving flu vaccine alone (FIG. 14d).

The Mechanism of NAFL/IMIQ Adjuvant

To determine the underlying mechanism, we tracked MHC II$^+$ cells at the inoculation site with or without laser treatment in mice expressing MHC II infused with green fluorescent protein (GFP). The MHC II$^+$ cells in the skin are mainly DCs, Langerhans cells, and macrophages, broadly defined as APCs. An increase in the motility of APCs was noticed soon after laser treatment and these cells were gradually recruited to the vicinity of MTZs. Their accumulation around individual MTZs became apparent as early as 3 hours and peaked 24 hours after laser illumination (FIG. 15a, upper panel). As expected, the MTZ-induced recruitment of APCs was well separated spatially (FIG. 15a, left panel). Topical IMIQ alone did not stimulate any accumulation of these GFP$^+$ cells, similar to untreated controls. To our surprise, IMIQ did not augment, but reduced NAFL-induced accumulation of APCs (FIG. 15a, lower panel), raising an intriguing possibility that IMIQ might promote emigration of APCs. In an attempt to address this, whole mount histology of the inoculation site was performed to determine entrance efficiency of APCs into the lymphatic vessels. It was found that the number of GFP$^+$ cells in the lymphatic vessels was significantly increased by IMIQ and to a lesser extent, by NAFL, but it was the combination that led to the highest number of APCs entering into the lymphatic vessels among all the groups at all time points tested (FIG. 15b, c). Consistent with a highest number of GFP$^+$ cells in the lymphatic vessels was a lowest percentage of CD11c$^+$ DCs in the skin, in parallel to a corresponding increase in the number of CD11c$^+$ DCs in the draining lymph nodes (dLNs) in mice receiving the vaccine and the NAFL/IMIQ adjuvant (FIG. 15d, e). Accelerated emigration of APCs to dLNs can be crucial at two fronts: (1) augmentation of flu vaccine-induced immunity and (2) reduction of local inflammation because a smaller number of matured APCs at the inoculation site can speed up inflammation resolution, whereas a higher number of matured DCs in the dLNs are pivotal for heightened immune responses.

CD11c$^+$ cells only increased in ipsilateral lymph nodes but not in contralateral lymph nodes indicating that the adjuvant effect of NAFL/IMIQ impacts locally rather than systemically. Therefore we focused on local events to identify the underlying mechanism of synergistic adjuvant effect of NAFL and IMIQ. The active recruitment of APCs around each MTZ promoted us to study local chemokine production stimulated by NAFL treatment. Six out of nine chemokines examined were elevated after 6 hours of NAFL treatment, peaked in 24 hours, and dwindled down thereafter (FIG. 16a), in agreement with resolving inflammation at the inoculation site in 2 days (FIG. 13c). Among these chemokines, CCL2, CCL20, CXCL9, CXCL10, CXCL12 and Chemerin are known to preferably attract pDCs. In accordance with this, NAFL treatment resulted in 4-fold more pDCs at the inoculation site in 24 hours (FIG. 16b), which were recognized as CD11c$^+$CD11b$^-$B220$^+$Ly6C$^+$PDCA-1$^+$ cells by flow cytometry. pDC recruitment was further augmented by topic IMIQ leading to an 8-fold increase in the percentage of pDCs at the inoculation site (FIG. 16b). The pDCs appeared to mainly accumulate in the vicinity of MTZs as evidenced by strong immunohistological staining with an antibody directed at a pDC-specific maker, Siglec H around each MTZ (FIG. 16c, upper). NAFL/IMIQ might also attract other immune cells, but pDCs were preferable targets of IMIQ because of a high level TLR7 expression on the cells. Preferable mobilization of pDCs was consistent with Th1-skewed immunity mounted by NAFL/IMIQ adjuvant. Upon activation by IMIQ, pDCs, but not conventional DCs, produced high levels of proinflammatory cytokines like TNF-α, IL-6, and Type I interferon-α/β (IFNα/β). This cytokine production profile of pDCs following IMIQ stimulation helps us understand a relatively high level of IFN-α/β, TNF-α, IL-6, and IL-12 in the inoculation site 6 hours after the immunization in the presence of NAFL/IMIQ adjuvant (FIG. 16d). In contrast, IMIQ alone failed to vigorously increase the expression of these cytokines under similar conditions, in agreement with previous investigation.

Among these cytokines induced at the inoculation site, TNF-α has been demonstrated to enhance emigration of dermal DCs into dLNs. We thus ID injected a TNF-α inhibitor, soluble TNF-Receptor Type I (TNF RI) into the inoculation site following the immunization. The inhibitor hampered adjuvant effects of NAFL/IMIQ, in particular, on IgG2a production (p<0.001, t-test), highlighting a critical role for TNF-α in NAFL/IMIQ-mediated adjuvanicity. Moreover, the adjuvanicity of NAFL/IMIQ in Th1 immunity was impaired in mice deficient in IFN regulatory factor7 (IRF7−/−), suggesting contribution of IFN-α/β, two major activators of immature DCs to the immune-enhancement of NAFL/IMIQ as well. The Th1-predominant cytokine milieu at the inoculation site was pivotal for increasing percentages and numbers (FIG. 16e, f) of CD40$^+$ and CD86$^+$ mature CD11c$^+$ DCs in the dLNs in the presence of NAFL/IMIQ as compared to the presence of either adjuvant or absence of any adjuvant. This increase in mature DCs was consistent with increased mean fluorescent intensity (MFI) of CD40 and CD86 staining on the cells. Notably, the percentages of CD40$^+$ and CD86$^+$ DCs increased significantly in the IMIQ group at 6 or 18 hours or in the NAFL group in 6 hours after immunization, but the total number of matured DCs in the dLNs were much more prominent in the NAFL/IMIQ group, which were directly relevant to the strong acquired immunity in the animals (FIG. 16e, f). Strikingly, not all proinflammatory cytokines were synergistically elevated by NAFL/IMIQ, and rather, IL-1 family (IL-1α/β, IL-18, IL-33) and thymic stromal lymphopoietin (TSLP) were diminished considerably as compared to mice immunized with the vaccine alone, or along with either topical IMIQ or NAFL (FIG. 16d). The selective decrease in these mediators may be another reason behind a limited local reaction in the presence of NAFL/IMIQ, because both IL-1 family and TSLP are mediators of local inflammation and dermatitis as demonstrated by a number of studies.

To directly address a pivotal role of pDCs in the synergistic adjuvant effect of NAFL and IMIQ, we depleted pDCs in Balb/c mice by injections of anti-mPDCA-1 antibodies prior to immunization as previously described. pDC depletion did not affect IgG1 levels, but profoundly impaired IgG2a production in the NAFL/IMIQ group (FIG. 16g upper panel, p<0.01 t-test). Consistent with diminished IgG2a titers, pDC depletion also greatly compromised cell-mediated immune responses, reflected with significant decreases in the percentages of CD4$^+$ and CD8$^+$ T cells secreting INF$_{-γ}$ (FIG. 16g middle and lower panels, p<0.01 t-test). Interestingly, the impairment was not evidenced in IMIQ group indicating that the effect of topical IMIQ relied primarily on dermal resident APCs, like dermal DCs, not pDCs that were almost not detectable in normal skins. In contrast to IMIQ, NAFL adjuvant appeared to depend on pDCs in augmentation of cellular mediated immune responses. pDC depletion resulted in a significant decrease in the percentages of both CD4$^+$ (p<0.01 t-test) and CD8$^+$ T (p<0.05 t-test) cells producing IFN$_{-γ}$, in mice immunized with NAFL-adjuvanted flu vaccine (FIG. 16g). The results argue strongly that NAFL-mediated recruitment of pDCs into the inoculation site from circulation is the key for the observed adjuvant effect of NAFL/IMIQ.

Augmentation of Flu Vaccine in Aged Mice

Given the strong cell-mediated immune response evoked by the new adjuvant, we extended our investigation to old mice, because the elderly respond to current seasonal flu vaccine poorly. Yet, it is this population who suffers from a highest level of morbidity and mortality after flu infection and need the vaccine most. As can be seen in FIG. 17a, BALB/c mice at 18 months of age elicited a rather weak immune response compared with that of adult mice after IM immunization with flu vaccine alone. The weak immune response was apparently not improved by ID vaccination regardless of whether NAFL or IMIQ was employed, which explains why ID flu vaccine is not currently approved for dose-sparing in the elderly. In contrast, the presence of NAFL/IMIQ adjuvant elicited vigorous humoral ($p<0.001$, ANOVA/Dunnett's) and cellular ($p<0.01$, ANOVA/Dunnett's) immune responses in the animals (FIG. 17a-c). The levels of humoral and cell mediated responses were even greater than those provoked by AddaVax adjuvanted flu vaccine or in adult mice IM immunized with the same amount of flu vaccine (FIG. 17a-c, $p<0.01$, ANOVA/Dunnett's). Similar to adult mice, the NAFL/IMIQ adjuvant increased pDCs in number at the inoculation site and provoked primarily Th1 immune response in old mice as suggested by a robustly higher ratio of IgG2a to IgG1 and greater percentages of $IFN_{-\gamma}$-producing $CD8^+$ and $CD4^+$ T cells in the presence vs. the absence of NAFL/IMIQ adjuvant (FIG. 17b, c). As a result, ~80% (10/13) of the old mice were protected from lethal H1N1 viral infection after ID immunization of the flu vaccine with the NAFL/IMIQ adjuvant, which was clearly superior to the 17% (⅙) protection in the mice IM immunized with squalene-adjuvanted flu vaccine (FIG. 17d, e). All mice in other groups died of the viral challenge when the mice were ID immunized with flu vaccine alone or with either adjuvant (FIG. 17d, e).

Discussion

Many vaccine adjuvants are being developed in preclinical studies or in various stages of clinical trials and the potency of these conventional adjuvants often comes at a great expense of safety. In markedly contrast, the current investigation explores a novel adjuvant that limits adverse effects locally and systemically while augmenting efficacy of flu vaccines over the vaccine alone or squalene-adjuvanted flu vaccines. Another advantage of this adjuvant is its standalone feature, like a topical adjuvant, which means neither pre-mixture nor re-formulation is required to extend it to any existing or new vaccines. Other TLR agonists may be employed in place of or in combination with IMIQ. The hand-held, small laser device is self-applicable and FDA approved for facial wrinkle removal at home, which requires a much higher stringent safety standard than laser illumination of a tiny spot on the upper arm for vaccination. The laser parameters in the pig study are well below those normally used in a clinical practice for skin resurfacing, and can be readily incorporated into the existing proprietary design of the small device. The 1410 nanometer light works on a stamp/scanning fashion and is equally effective regardless of skin colors, in contrast to the 532 nanometer laser adjuvant described previously. Its microprobe is tightly sealed by a thin plastic that prevents any skin materials from contaminating the probe, and the sealer is readily cleaned aseptically to prevent person-to-person contamination. The laser does not damage the stratum corneum or the most out layer of epidermis so that the integrity of skin barrier is preserved (FIG. 13c). In addition to the super safety, the adjuvant can be readily incorporated with various needle-free, painless, microneedle-array patches for self vaccination. IMIQ cream Aldara was initially approved by the FDA more than 15 years ago as a topical treatment for genital/perianal warts at age 12 or older. The drug has also been approved for treatment of superficial basal cell carcinoma and actinic keratosis as of 2004. In those treatments, the cream is applied three times a week for up to 12 weeks or daily for several weeks, and in many cases a relatively large area of the skin is affected. In contrast, IMIQ is topically applied only once to a skin area of smaller than 1 $cm^2$, and thus the systemic absorption or local reaction is extremely limited. A combination of NAFL and topical IMIQ apparently alleviates, rather than worsening, skin irritation provoked by flu vaccine as shown in FIG. 14. NAFL/IMIQ not only blunts local inflammation but also raises little circulating IL-6 or body fever over flu vaccines. In contrast, a fever was clearly presented, concurrent with a significantly higher level of IL-6 in mice receiving IM vaccination of squalene-adjuvanted vaccines. If the same is confirmed in humans, the adjuvant may greatly increase patient-compliance because unpleasant fever following flu vaccination is one of the common reasons for people rejecting the vaccine.

The mechanisms underlying the ability of NAFL/IMIQ adjuvant to augment flu vaccine while reducing adverse events are likely to be multifaceted. Laser-damaged cells in each MTZ release danger signals that stimulate the production of a number of chemokines and preferably attract pDCs from circulation leading to their increased presence around each MTZ. These pDCs are then activated by IMIQ penetrating from the skin surface because the cells express a high level of TLR7. Upon activation they secrete TNF-α, IFN-α/β and the like, and these cytokines direct maturation and differentiation of APCs in situ, and accelerate trafficking of these matured APCs into the dLNs via lymphatic vessels. NAFL-induced recruitment and IMIQ-mediated activation are likely to be the primary mechanisms for the observed synergy of these two adjuvants, resulting in a high level of TNF-α secretion at the inoculation site. An essential part of TNF-α in maturation and emigration of dermal DCs into dLNs was clearly demonstrated by the ability of TNF-α inhibitor to impede immune enhancement of NAFL/IMIQ (FIG. 15b, c, d, e). Moreover, Cumberbatch et al. showed that ID injection of TNF-α evoked a concentration and time-dependent maturation and trafficking of dermal DCs into dLNs. On the contrary, mice deficient in TNF-α receptor had impaired DC maturation after bacterial infection. Besides TNF-α, IFN-α/β produced by pDCs also contributed to a high level of Th1 immunity evoked by NAFL/IMIQ. In IRF7 deficient mice whose pDCs could not produce IFN-α/β efficiently, the IgG2a titer was impaired, in agreement with a recent investigation. Moreover, depletion of pDCs almost completely blunted the adjuvant effect of NAFL/IMIQ on IgG2a production and on cell-mediated immune responses.

Another major finding of this investigation is that the micro sterile inflammation induced by the adjuvant occurs only briefly, peaking at 24 hours and subsiding in 48 hours, but this short period of local sterile inflammation appears sufficiently enough to educate DCs in bridging an innate to adaptive immune responses. The fast resolution of the inflammation at the inoculation site warrants the super safety of the approach. On the contrary, injection of Alum or MF59 stimulates persistent local inflammation at the inoculation site, which is however not necessary for their adjuvant effects. An elegant experiment conducted by Hutchison et at corroborated that prolonged alum-induced local inflammation was dispense for alum adjuvant. They found that alum-mediated enhancement in antigen presentation and DC activation occurred primarily in the first 24-48 hours. A surgical removal of alum-containing site of inoculation 2 hours after vaccination did not affect the adjuvanticity of alum, an argument strongly supported by the current investigation. The controllable sterile inflammation at the inoculation site via a micro-sterile inflammation array could thus become a gold standard for future safe adjuvant development. Besides a shortened period of local inflammation, infiltration of pDCs may also contribute to the reduced skin irradiation, as Gregorio et at reported that pDCs could rapidly infiltrate into skin in response of skin injury, and improve the skin recovery. Finally, a combination of laser and IMIQ selectively reduces the production of the cytokines of the IL-1 family and TSLP that are well known to contribute to the local skin irritation, which may be another mechanism for reducing local and systemic adverse events of this topical adjuvant.

The adjuvanticity of an ideal adjuvant should be localized and transient. Therefore, the finding that a strong immune response can be provoked by transient micro sterile inflammation at the inoculation site is of highly clinical significance for cutaneous vaccination. A growing body of evidence has shown that cutaneous vaccination is more effective than IM vaccination, as the skin is enriched in APCs and in networks of lymphatic vessels, in contrast to the muscle where few APCs reside. However, lack of a safe adjuvant for cutaneous vaccination hampers a broad application of this route of immunization, apart from inconvenience. Therefore, this micro sterile inflammation-based adjuvant merits clinic investigations for dose-sparing or augmenting flu vaccines in certain at risk groups like the elderly, with little concern of long term safety, because no any additive, apart from the vaccine itself is injected into the body.

Example 7

Figure Legends

FIG. 12—NAFL/IMIQ strengthens immunogenicity of ID flu vaccine: BALB/c mice were ID immunized with 0.06 µg (HA content) H1N1 flu vaccine alone (no adjuvant) or in the presence of NAFL, IMIQ, or NAFL/IMIQ adjuvant. For comparison, some mice were IM immunized with a same dose (IM) or a 10×higher dose (0.6 µg) of the vaccine. Humoral immune responses were measured in serum samples 4 weeks later including HAI titer (a), a total level of IgG (b), IgA (c) or IgG2a (d). HAI titers were further monitored at 4, 12, 24 and 36 weeks post immunization (e). A horizontal gray line indicates a standard protective titer of HAI. n=8, except NAFL and NAFL/IMIQ groups (n=10). (f, g) Cell-mediated immune responses. PBMCs were isolated one week after immunization, stimulated with the vaccine and anti-CD28 antibody and analyzed for the percentages of $IFN_\gamma$-secreting $CD8^+$ (f) and $CD4^+$ (g) T cells by flow cytometry. Non-immunized mice were used as controls. n=6, except NAFL and NAFL/IMIQ groups (n=8). (h j) Challenge studies. The immunized mice as well as non-immunized control mice were intranasally challenged with $10×LD_{50}$ of A/California/7/2009 H1N1 virus in 5 weeks post-immunization. The infected mice were euthanized 4 days post-infection to determine lung viral titers by $TCID_{50}$ assay using MDCK cells (h). n=6. Body weight (i) and survival (j) were monitored daily for 14 days. Percentages of body weight drop relative to a pre-infection level were compared between NAFL/IMIQ and NAFL or IMIQ groups before day 8 by t-test. Percentages of survivals were compared between NAFL/IMIQ and NAFL or IMIQ groups by Logrank test. n=6, except NAFL and NAFL/IMIQ groups (n=8). *, $p<0.05$; , $p<0.01$ or *, $p<0.001$, respectively.

Figure 13:
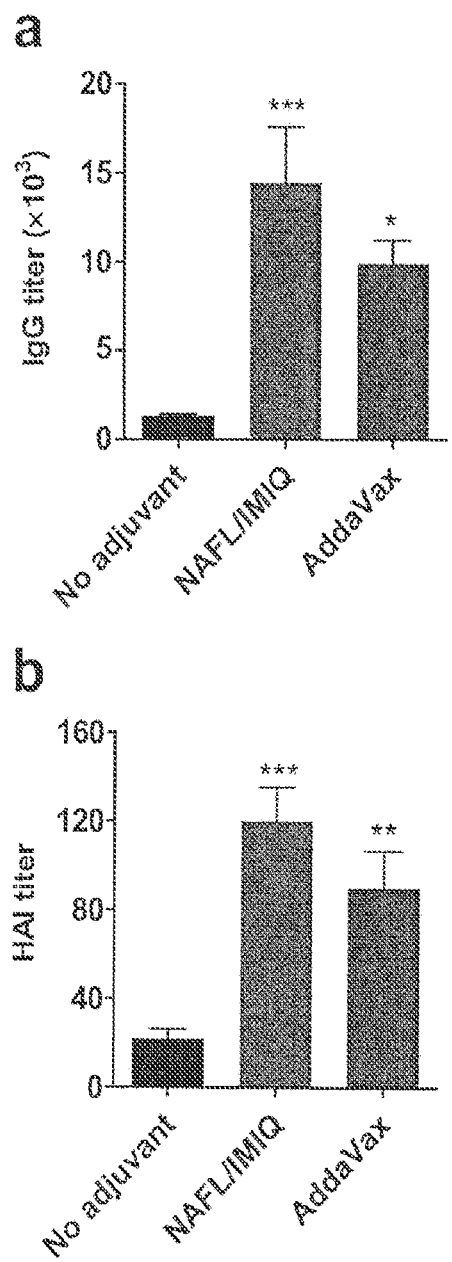
FIGS. 13A-13G are graphs that evidence a safer profile locally and systemically of a laser adjuvant of the invention as compared to a current clinic adjuvant MF59 (used in elderly).
Figure 13A:
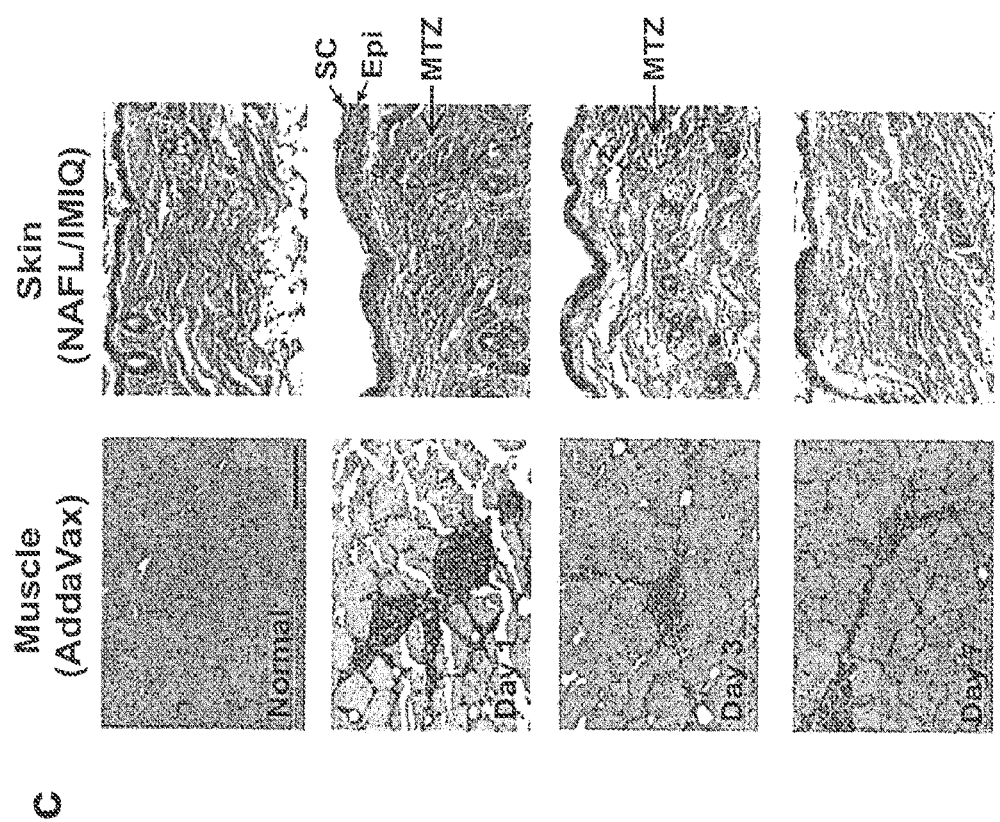
Figure 13B:
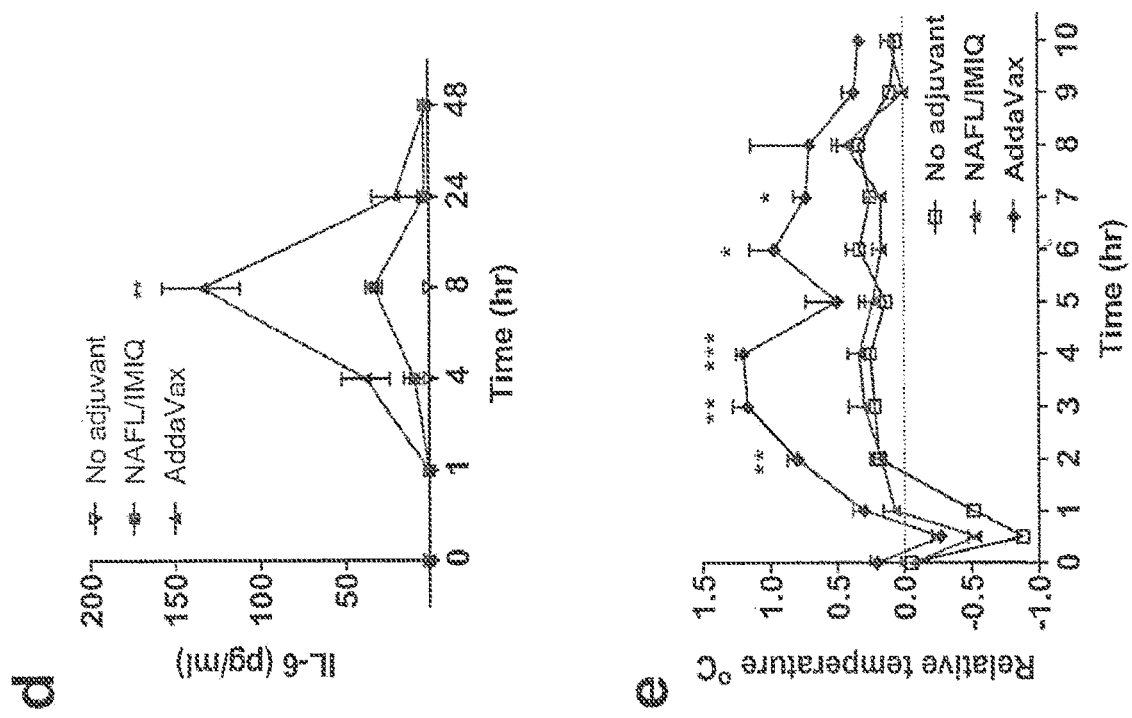

FIG. 13—A safer profile of NAFL/IMIQ over squalene-based adjuvant: BALB/c mice were ID immunized with flu vaccine alone (no adjuvant) or in the presence of NAFL/IMIQ adjuvant, or IM immunized with a same dose of the vaccine mixed with squalene-based adjuvant (AddaVax). Serum IgG (a) and HAI (b) levels were measured in 2 weeks. n=8. (c) Local inflammation shown with H&E staining Muscle and skin tissues of the inoculation sites were collected at days 1, 3, and 7, and representative results of 4 similar experiments performed are shown. Arrows and black dash lines indicate part of micro-thermal zone (MTZ), scale bar, 100 µm. Note: stratum corneum (SC) and epidermis (Epi) are in place after laser treatment. Serum IL-6 was measured at 0, 1, 4, 8, 24, and 48 hours after immunization by ELISA (d) and body temperature was monitored hourly for 10 hours (e). All temperatures were normalized to non-immunized mice. n=4. The experiments were repeated twice with similar results. *, $p<0.05$; , $p<0.01$ or *, $p<0.001$, respectively.

FIG. 14—NAFL/IMIQ adjuvant in swine study: The exterior hind legs of Yorkshire pigs were shaved, cleaned and ID vaccinated with 100 µl of the flu vaccine (3 µg HA content) (no adjuvant) or following one pass of laser illumination with Fraxel SR-1500 (NAFL), after which IMIQ was applied to the immunization site (NAFL/IMIQ). Alternatively, the immunization site receiving the vaccine alone was topically applied with IMIQ directly (IMIQ). Two weeks later, serum HAI titers were measured (a). Each symbol represents data from individual animals, and horizontal bars indicate the mean, and a dish line marks the standard protective titer of HAI. (b) Photos were taken right (day 0) and 1, 3, and 7 days after immunization with similar responses in 4 pigs in each group. Scale bar, 5 mm. (c) The erythema areas of injection sites were analyzed by Image Pro Premier software 3 days after immunization. Each symbol represents a mean value of one injection site analyzed for 3 times. (d) Representative H&E stained slides showing infiltrated cells at the inoculation site. Scale bar, 200 µm. *, $p<0.05$; , $p<0.01$ or *, $p<0.001$, respectively.

Figure 15:
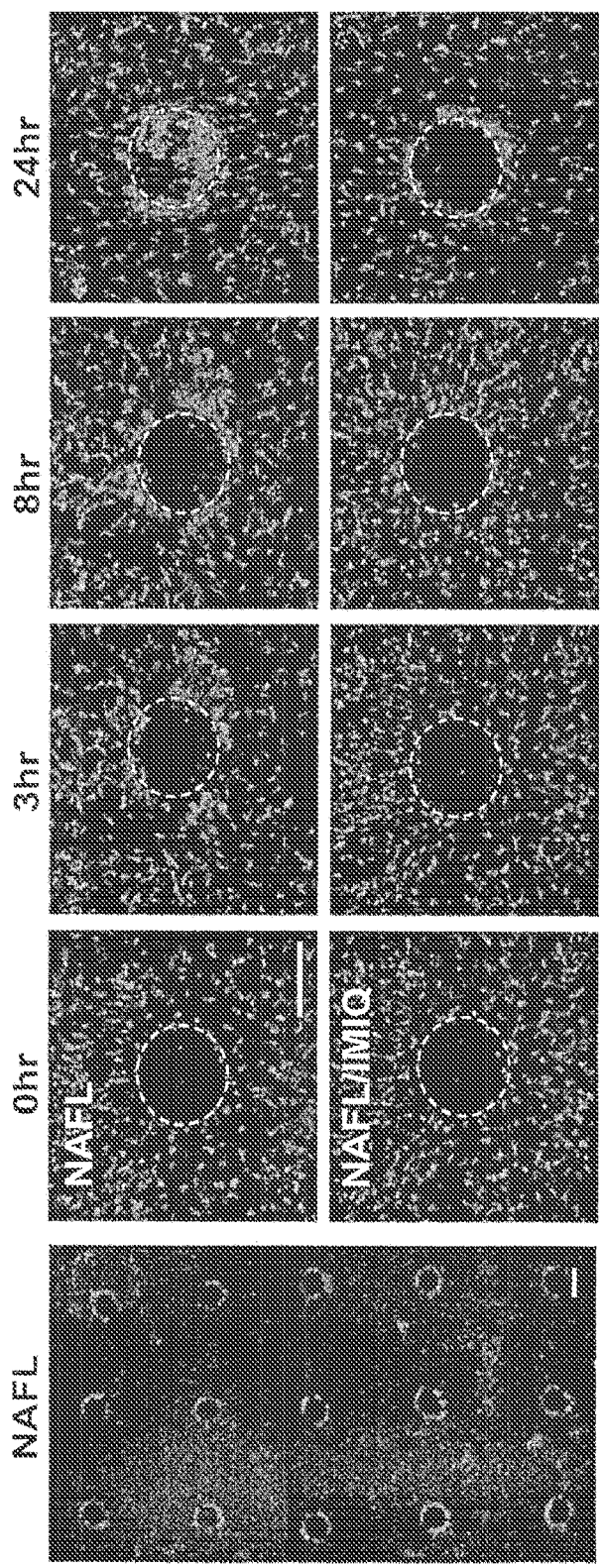
FIGS. 15A-15G are graphs from a mechanism study indicating that one subset of antigen presenting cells pDCs play a crucial role for the adjuvant effect.
Figure 15A:
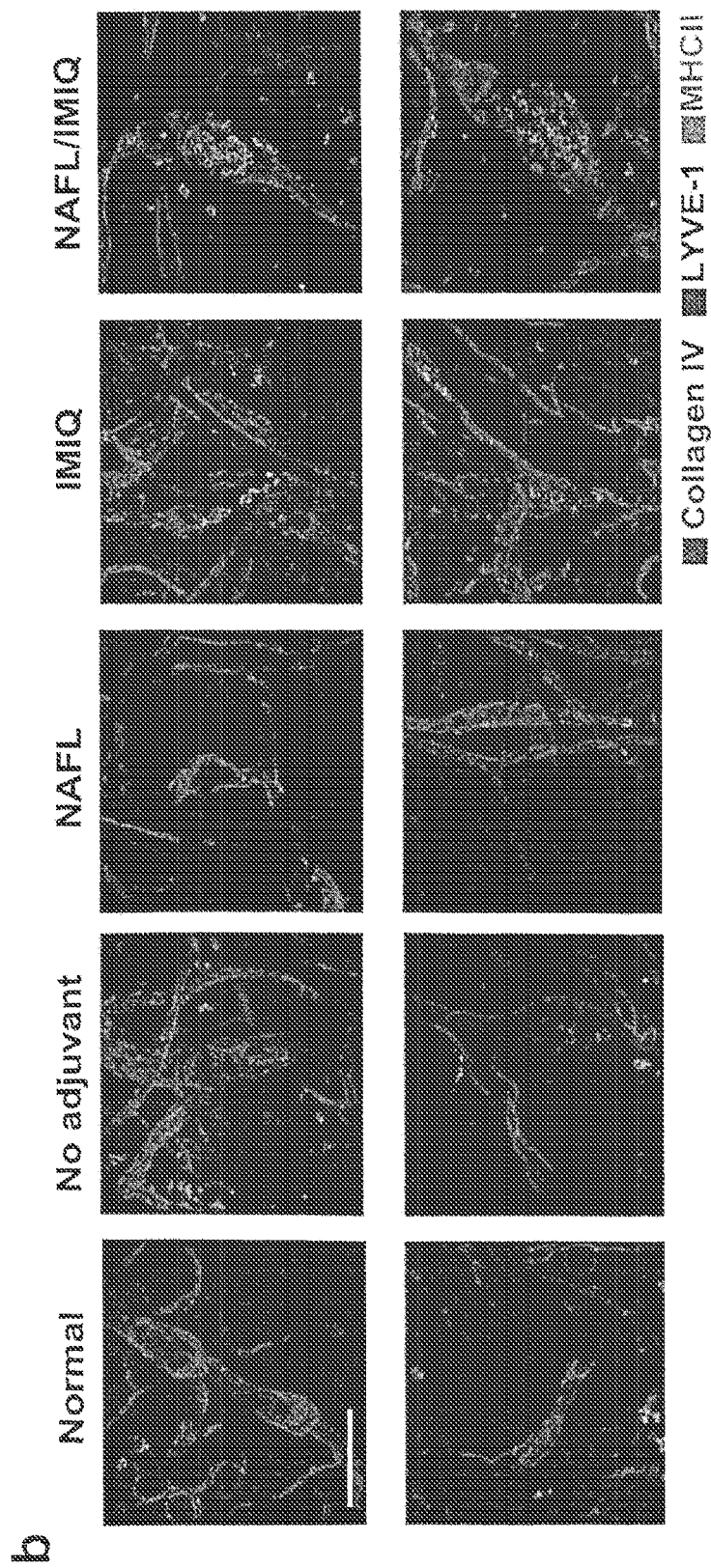
Figure 15B:
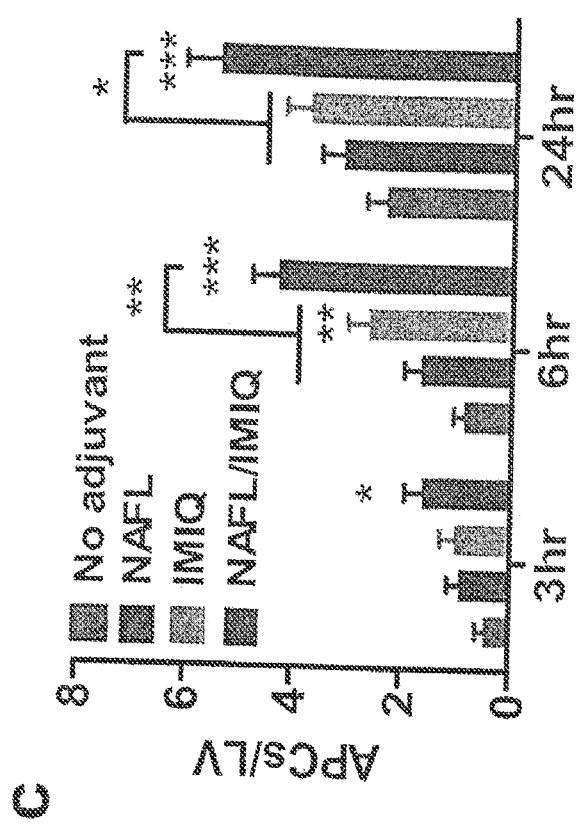
Figure 15C:
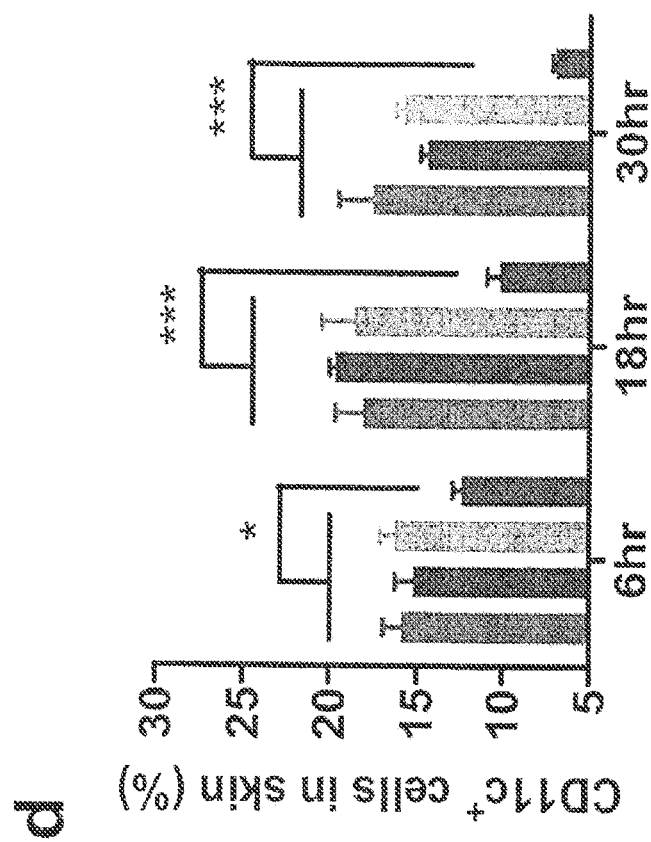
Figure 15D:
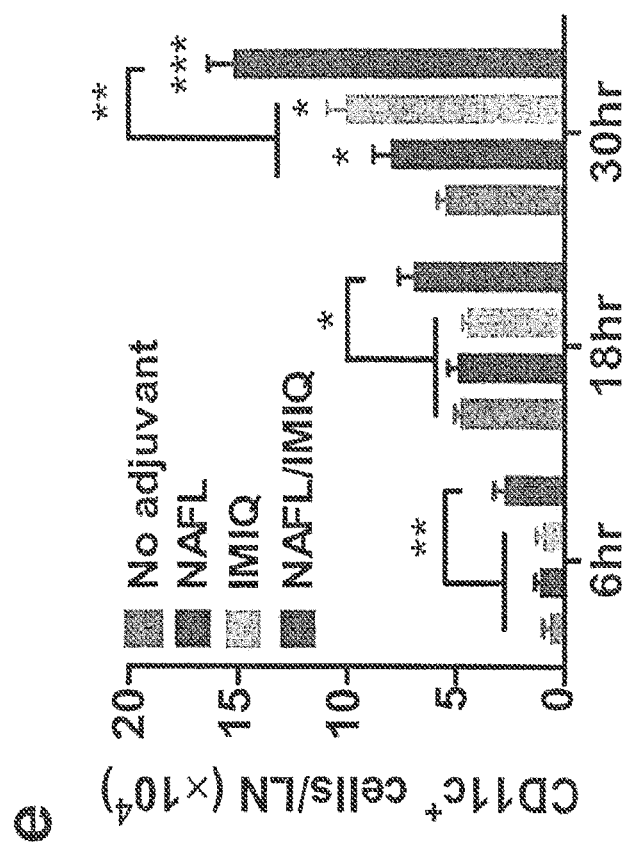

FIG. 15—Accelerated emigration of APCs into dLNs in the presence of NAFL/IMIQ: MHC II-EGFP transgenic mice were ID immunized in ear skin with flu vaccine adjuvantated with NAFL or NAFL/IMIQ. Accumulation of MHC II$^+$ APCs around individual MTZs was visualized by intravital confocal microscopy at varying times after immunization and the one captured at 8 hours was shown in (a), left panel. A representative MTZ was tracked at 0, 3, 8, 24 hours after immunization of flu vaccine with NAFL treatment (upper panel) or NAFL/IMIQ (lower panel) in (a), representative of 6 similar results in two separate experiments. White dash circles highlight MTZs. Scale bar, 200 µm. (b) Monitoring APCs within lymphatic vessels. Ears were prepared and stained by whole mount immunohistology 8 hours post-immunization. The APCs (green) and lymphatic vessels (blue and/or red) and blood vessels (red) were visualized by confocal microscopy, representative of 6 similar results in two separate experiments. Scale Bar, 100 µm. Average numbers of APCs within each lymphatic vessel were determined by manual counting GFP$^+$ cells inside the lymphatic vessels in 20 randomly selected fields with at least a total of 40 lymphatic vessels counted (c) during which three-D scanning was performed to confirm the intra-vessel localization of each APC (b). The basal level of APCs inside the lymphatic vessels in a non-immunization site was ~0.25 (data not shown). (d, e) Proportions of CD11$^+$ DCs in the skin (d) and a total number of DCs in each dLN (e). CD11c$^+$ DCs in the dorsal skin and dLNs were quantified by flow cytometry in BALB/c mice at indicated times after immunizing with the flu vaccine alone or in the presence of indicated adjuvants as FIG. 12. The basal level of CD11c$^+$ cells in non-immunization skin was ~15% and in lymph nodes was ~7×10$^3$/lymph node (data not shown). n=6, except NAFL/IMIQ group (n=8). *, p<0.05; , p<0.01 or *, p<0.001, respectively.

Figure 16:
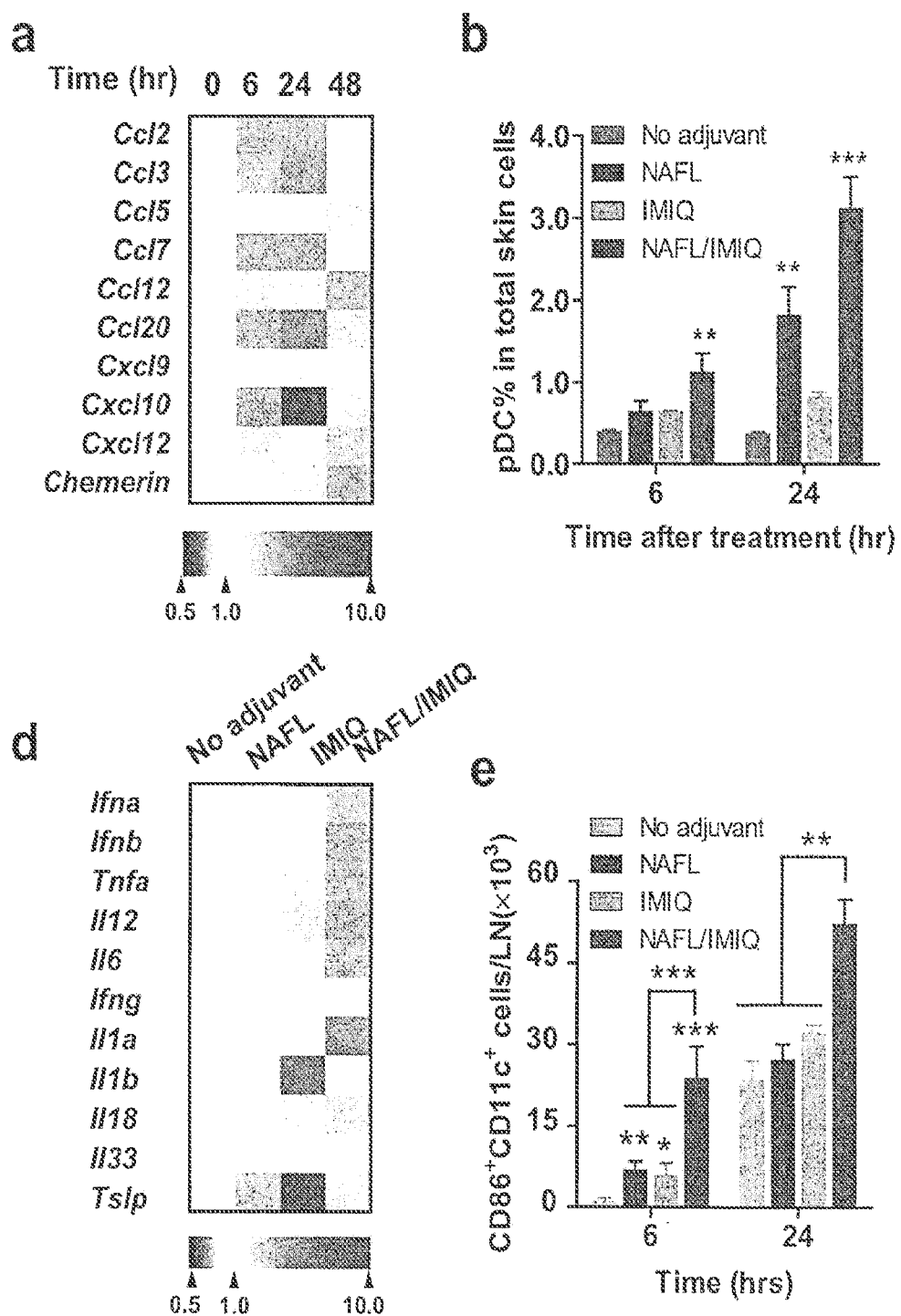
FIGS. 16A-16G are graphs from another mechanism study indicating that one subset of antigen presenting cells pDCs play a crucial role for the adjuvant effect.
Figure 16A:
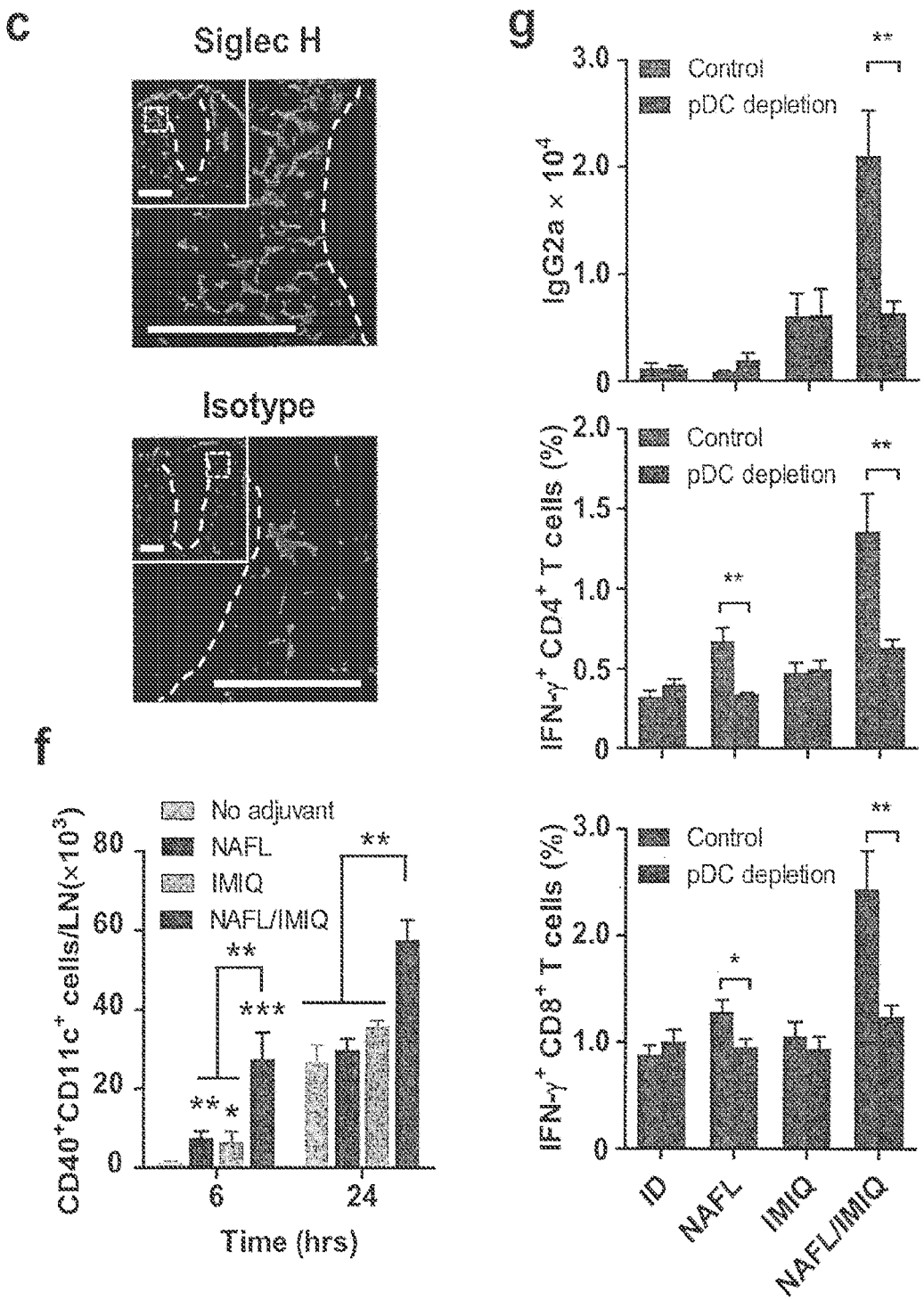

FIG. 16—NAFL/IMIQ preferably recruits pDCs.: (a) Chemokine production at the inoculation site. The levels of indicated chemokines were measured in BALB/c mice after varying times of laser treatment by real-time qPCR, normalized to GAPDH, and expressed as fold increases relatively to time zero. Each square represents the mean value of 4 mice and color indicates a fold increase from low (blue) to high (red) as illustrated at the bottom. (b) Recruitment of pDCs into the inoculation site. pDCs were identified by B220$^+$CD11b$^-$PCDA-1$^+$Ly6C$^+$ cells by flow cytometry and the percentages of pDCs in total skin cells were determined 6 and 24 hours after vaccination with flu vaccine alone or in the presence of indicated adjuvants. n=4. (c) The inoculation sites were also immunofluorescently stained with Siglec H-specific antibody after 24 hours of NAFL/IMIQ treatment. Siglec H-specific pDCs (red) were greatly concentrated around each MTZ (white dish lines) (upper panel) and no pDC staining was seen with isotype control (lower panel). Representative results of 6 similar samples in two separate experiments. Blue, DAPI staining of cell nuclei and scale bar, 100 μm. Insets in (c) show a MTZ and part of the MTZ that is enlarged is outlined by white dish line. (d) Cytokine expression at the inoculation sites 6 hours after immunization. The expression levels of indicated cytokines were measured by real-time qPCR as above and expressed as fold increases relative to those in the mice receiving no adjuvant. Each square is the mean value of 4 mice and cytokines tested are IFN-α (Ifna), IFN-β (Ifnb), TNF-α (Tnfa), IL-12 (Il12), IL-6 (Il6), IFN-γ (Ifng), IL-1α (Il1a), IL-1β (Il1b), IL-18 (Il18), IL-33 (Il33), TSLP (Tslp). (e, f) Increasing numbers of matured DCs in dLNs in mice receiving flu vaccine and NAFL/IMIQ. dLNs were collected at indicated times after immunization and matured DCs were identified by anti-CD86, anti-CD40 and anti-CD11c antibodies and expressed as numbers of CD86$^+$CD11c$^+$ cells (e) or CD40$^+$CD11c$^+$ cells (f) per lymph node. n=6, except NAFL/IMIQ group (n=8). (g) Effect of pDC depletion on NAFL/IMIQ adjuvanicity. Mice were i.p. injected with 400 μg PDCA-1 antibody to deplete pDCs or control antibodies (control) at 24 and 0 hour before immunization. One week later cellular immune responses were measured (middle and lower panel), and humoral immune responses were measured two weeks later (upper panel). n=8. *, p<0.05; , p<0.01 or *, p<0.001, respectively.

Figure 17:
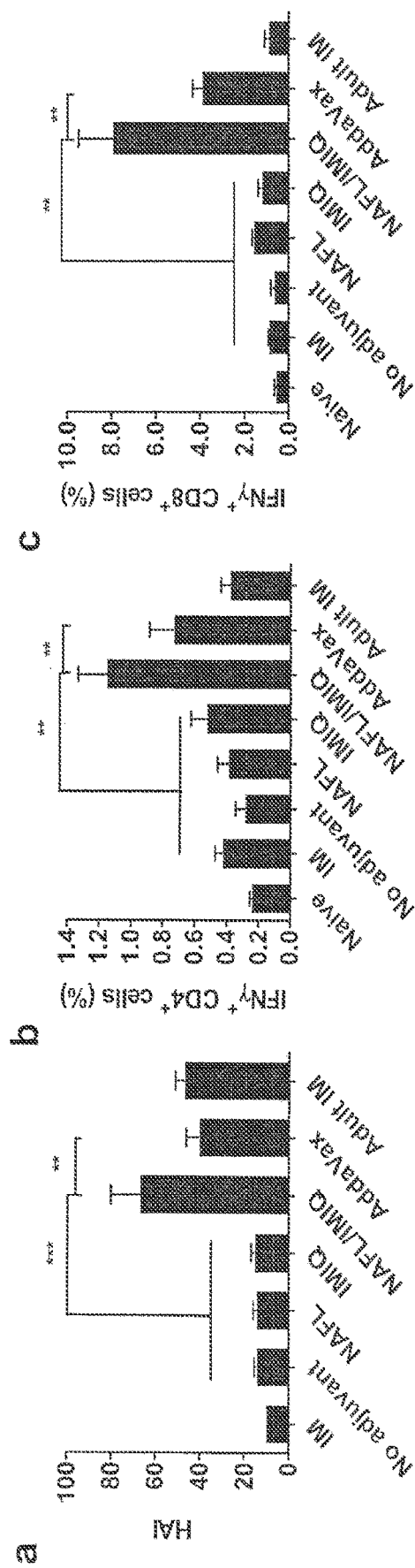
FIGS. 17A-17E are graphs that evidence NAFL/IMIQ greatly augments protective immunity in old mice.
Figure 17A:
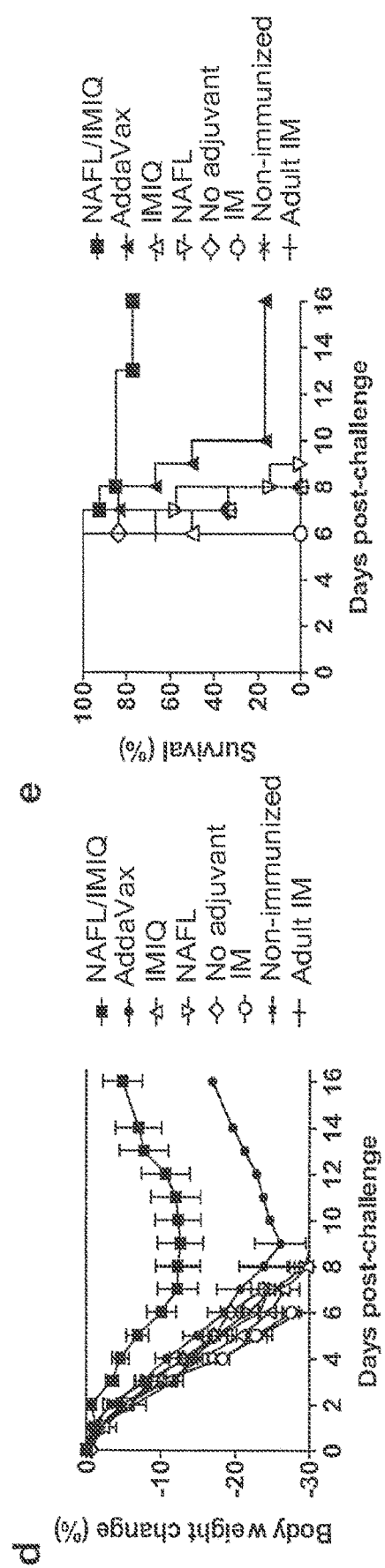

FIG. 17—NAFL/IMIQ greatly augments protective immunity in old mice: Old BALB/c mice were ID immunized with 0.6 μg H1N1 flu vaccine alone or in the presence of NAFL, IMIQ, or NAFL/IMIQ adjuvant. IM immunizations with a same dose of the vaccine mixed with AddaVax adjuvant in old mice or without AddaVax (AddaVax) in both old (IM) and adult (adult IM) mice were used as controls. Four weeks later, serum HAI antibody titer was measured (a). Percentages of IFN$_\gamma$-secreting CD4$^+$ (b) and CD8$^+$ (c) T cells were analyzed in vaccine-stimulated PBMCs one week after the immunizations. Five weeks after immunization, mice were challenged with 5×LD$_{50}$ of mouse-adapted A/California/7/2009 H1N1 viruses. Body weight (d) and survival (e) were monitored daily for 16 days after challenge. n=6, except NAFL/IMIQ group (n=13). *, p<0.05; , p<0.01 or *, p<0.001, respectively.

Materials and Methods

Animals

Inbred BALB/c mice and outbred Swiss Webster mice at 6-8 weeks of age were purchased from Charles River Laboratories. Mice of both genders were used randomly with no notable difference. Eighteen-months-old BALB/c mice (old mice) were purchased from National Institute of Aging (NIA). Irf7−/− mice on C57BL/6J background were a kindly gift of Tokyo University and C57BL/6J control mice were obtained from Jackson Laboratories. MHC II-EGFP mice expressing MHC class II molecule infused into enhanced green fluorescent protein were a kindly gift of Harvard Medical School. Yorkshire pigs at 4 months of age were obtained from the Teaching and Research Resources at Tufts University. The animals were housed in the pathogen-free animal facilities of Massachusetts General Hospital (MGH) in compliance with institutional, hospital, and NIH guidelines. All studies were reviewed and approved by the MGH Institutional Animal Care and Use Committee.

Laser Adjuvant

A FDA-approved, home-use PaloVia laser was used in mice (PaloVia Skin Renewing Laser, Palomar Medical Technologies). The hand-held device emits a 1410-nanometer laser light and two passes at the medium power were used to generate overlapped MTZs at the inoculation site. Pigs were treated with one pass of Fraxel SR-1500 laser (Solta Medical) which produced a laser with 17% coverage, 93 MTZs/cm$^2$/pass and 35 mJ/microbeam.

Flu Virus And Vaccine

Pandemic A/California/7/2009 H1N1 flu virus was obtained from American Type Culture Collection (ATCC, #FR-201). The virus was expanded in 10-day-old embryonated chicken eggs at 35° C. for 3 days, harvested by ultracentrifugation, and frozen at −80° C. until use. Its quantity was determined with a 50% tissue culture infectious dose (TCID$_{50}$) in Madin-Darby canine kidney (MDCK, ATCC, #CCL-34) cells. To challenge mice, the virus was adapted in mice for three cycles of intranasal instillation-lung homogenate preparation and infectivity of the resultant virus was assayed by a 50% lethal dose (LD$_{50}$) in adult BALB/c mice following a standard protocol. Monovalent A/California/7/2009 H1N1 flu vaccine (Sanofi Pasteur, Inc.) was obtained from MGH pharmacy and BEI Resources, used at 0.06 μg/mouse or 3 μg/pig unless otherwise indicated.

Immunizations and Challenges

Mice to be immunized were hair removed on the lower dorsal skin and ID inoculated next day with flu vaccine (ID) or illuminated with laser before flu or indicated vaccines were ID administered. After ID immunization, the inoculation site was either left alone or topically applied of Imiquimod cream (Aldara, 3M Pharmaceuticals). The inoculation site was then covered with a 3M Tegaderm film to protect it. For IM injection of adjuvanted flu vaccine, AddaVax®, a squalene based nano-emulsion adjuvant (Invivogen) with a formulation similar to commercial adjuvant MF59, was mixed at 1:1 ratio with flu vaccine (total volume 20 μl) and IM injected. Body temperature was monitored hourly after immunization in some of the mice by a temperature control device (FHC, ME). The immunized and control mice were challenged by intranasal instillation of $10 \times LD_{50}$ mouse-adapted 2009 H1N1 viruses. Body weight and survival were monitored daily for 14 days unless otherwise specified. In some infectious experiments, lungs were harvested 4 days after challenge to measure lung viral titer by $TCID_{50}$ assay. To immunize pigs, the animals were anesthetized by IM injection of telazol (2.2 mg/kg)/xylazine (2.2 mg/kg)/atropine (0.04 mg/kg) and maintained under isoflurane (2-3%) inhalation during hair removal and immunization. Immunization procedure was similar as described in mice with 100 μl flu vaccine (3 μg HA content) inoculated into the exterior hind leg skin either alone or in the presence of NAFL, IMIQ, or NAFL/IMIQ adjuvant. To quantify local skin reactions, the inoculation sites were photographed and the erythema area at each inoculation site was circled and analyzed by Image Pro Premier software (Media Cybernetics, Inc.) for 3 times. Mean erythema area of each inoculation site was presented.

HAI Assay

HAI titers were assayed according to a published protocol (PMID: 19274084). Briefly, serum samples were incubated with receptor-destroying enzyme (RDE) (Denka Seiken, Tokyo, Japan) at 37° C. overnight followed by heat inactivation at 56° C. for 30 minutes. The resultant serum samples were incubated with 4 hemagglutination (HA) units of flu virus at 37° C. for 1 hour after serial dilutions, and then with 0.5% chicken red blood cells (Charles River Laboratories) at room temperature for 30 minutes. The HAI titer was defined as the reciprocal of the highest dilution that inhibited hemagglutination.

ELISA

Vaccine-specific IgG, IgG1, IgG2a and IgA antibody titers were measured by enzyme-linked immunosorbent assay (ELISA). In brief, 1 μg/ml recombinant HA was coated onto ELISA plate in $NaHCO_3$ buffer, pH 9.6. After incubation with serially diluted serum samples, HRP-conjugated goat anti-mouse IgG (NA931V), IgG1 (A90-105P), IgG2a (61-0220) or IgA (A90-103P) antibody was added to measure specific subtypes. For C57BL6 mice, anti-mouse IgG2c (1079-05) antibody was used in place of anti-IgG2a antibody.

Cell-mediated Immune Responses

One week after immunization, small blood samples were collected from immunized and control mice in a heparinized tube by tail vein bleeding. Peripheral blood mononuclear cells (PBMCs) were isolated after red blood cell lysis. PBMCs ($10^6$ cells/ml) were incubated with flu vaccine (1 μg/ml HA content) and anti-CD28 (37.51) antibody (4 μg/ml) overnight. Golgi-Plug was added to prevent cytokine secretion in the additional 5 hours of the incubation. The stimulated cells were stained with fluorescence conjugated anti- CD4 (RM4-5), -CD8 (53-6.7), and -$IFN_\gamma$ (XMG1.2) antibodies and subjected to flow cytometric analysis as previously reported.

Histological Examination

Mice were ID immunized with flu vaccine in the presence of NAFL/IMIQ adjuvant or IM with the vaccine mixed with AddaVax. One, three or seven days later, the tissues at the inoculation site were dissected, fixed and stained by a standard H&E procedure. Similar histological examination was carried out in pigs after 3 days of immunization. The slides were scanned and analyzed by NanoZoomer (Hamamatsu).

Intravital Confocal Imaging

The ear of MHC II-EGFP transgenic mice was treated by NAFL or NAFL/IMIQ. $GFP^+$ cells in epidermis and dermis were imaged by intravital two-photon confocal microscopy (Olympus FV-1000) as described. Three-D reconstruction was used to visualize accumulation of $GFP^+$ cells around individual MTZs by Image J software.

Whole Mount Immune Histology

The ear of MHC II-EGFP transgenic mice was immunized with flu vaccine in the presence of the indicated adjuvants. The outer ear flaps were prepared at indicated times post-immunization, fixed by 4% formaldehyde at 4° C. overnight, and blocked by 2% FBS/PBS for 2 hours at room temperature. The fixed samples were reacted with rat anti-LYVE-1 (223322) antibody to identify lymphatic vessels and rabbit anti-Collagen IV (ab6586) antibody at 4° C. overnight to label both lymphatic and blood vessels, after which the samples were stained with Cy3-conjugated anti-rat (A10522) and NL637-conjugated anti-rabbit (NL005) antibodies at 4° C. overnight. The stained samples were mounted and imaged by two-photon confocal microscopy (Olympus FV-1000).

Immunohistological Analysis of pDCs

The lower dorsal skin of mice was exposed to NAFL/IMIQ adjuvant. Twenty four hours later, full thickness of the skin at the site of laser illumination was excised, and frozen tissue sections were prepared and stained by anti-mouse Siglec H (440c) or isotype control antibody and DL594 goat anti-rat IgG (SA5-10081) antibody. The slides were mounted with DAPI contained mount medium, and imaged by confocal microscopy.

Analysis of Dermal DCs or pDCs by Flow Cytometry

Skin at the inoculation site was excised, minced, and digested with Dispase II (Invitrogen, NY) and Collagenase D (Roche, Ind.) for 2 hours at 37° C. The digested skin tissues were passed through a 100 μm cell strainer to prepare single cell suspensions. The resultant cells were treated with anti-CD16/CD32 (93) for 20 minutes, followed by staining with the following fluorescence antibodies for 30 minutes on ice: APC-anti-PDCA-1(927), PE-anti-CD11c (N418), BV421-anti-CD11b (M1/70), FITC-anti-MHCII (M5/114.15.2), FITCanti-Ly6C (HK1.4), APC/Cy7-anti-B220

(RA3-6B2). The stained cells were acquired on a FACSAria (BD) and analyzed using FlowJo software (Tree Star).

In Vivo Depletion of pDCs

Balb/c mice were i.p. injected with Anti-mPDCA-1 (JF05-1C2.4.1, Miltenyi Biotec Inc.) antibody (400 µg/mouse/time) twice at 24 and 0 hours before immunization as previously described. The depletion efficiency was confirmed by flow cytometry of pDCs in the blood samples. The cellular immune responses were analyzed one week later, and humoral immune responses were analyzed two weeks after immunization.

Quantification of DCs in dLN dLNs were collected and single-cell suspensions were prepared, counted, stained with FITC-anti-CD11c (N418), APC-anti-CD40 (3/23) and PerCp-Cy5.5-anti-CD86 (GL-1) antibodies and analyzed by flow cytometry as previously described. Total $CD11c^+$ cells and $CD40^+$ and $CD86^+$ $CD11c^+$ cells per LN were calculated in the basis of the total LN cell number and percentages of each cell subsets.

Quantitative Real-Time PCR

To analyze chemokine and inflammatory cytokine expression at the inoculation site, the full thickness of the skin area about $7 \times 10$ mm$^2$ was excised, and total RNA was extracted, reverse-transcribed, and amplified by real-time qPCR using a SYBR Green PCR kit (Roche, Ind.). GAPDH was used as an internal control. All the primers were synthesized at MGH DNA core.

Statistical Analysis

Two tailed t-test (t-test) was used to analyze a difference between two groups, and one way ANOVA was used among multiple groups. ANOVA followed by Bonferroni correction (ANOVA/Bonferroni) was used to compare selected pairs, and ANOVA followed by Dunnett's test (ANOVA/Dunnett's) was for comparing all groups with control group. The appropriate nonparametric tests were used if data failed to meet assumptions for parametric statistics. P value was calculated by PRISM software (GraphPad, CA) and a difference was regarded significant if p was less than 0.05. No animals were excluded from the analysis. The investigators were not blinded to the experiments which were carried out under highly standardized and predefined conditions, except for photo analysis and H&E slide examination.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention. All patents and publications cited herein are incorporated herein by reference in their entireties.

What is claimed is:

1. A method of vaccinating a mammalian subject, the method comprising:
   arranging a source of electromagnetic radiation on or proximate to a target injection site of skin of the mammalian subject;
   controlling the source of electromagnetic radiation to deliver a dose of electromagnetic radiation to the target injection site determined to create at least one thermally-denatured zone in the target injection site; and
   intradermally injecting a vaccine within the target injection site to vaccinate the mammalian subject, and
   wherein an immune response in the mammalian subject is improved following the intradermal injection as a result of the creation of the at least one thermally-denatured zone in the target zone.

2. The method of claim 1, wherein a width of the at least one thermally denatured zone is less than 1 millimeter.

3. The method of claim 1, wherein the at least one thermally denatured zone comprises columns having thermally denatured epidermal and dermal tissue and a stratum corneum that is not denatured, and wherein the columns are spatially separated from one another by an unirradiated area of skin.

4. The method of claim 3, wherein a fractional surface coverage of the target zone by the at least one denatured zone is between 5% and 40%.

5. The method of claim 1, wherein the source of electromagnetic radiation includes at least one of a non-ablative laser, a diode laser, a fiber laser, a flashlamp, and a solid state laser.

6. The method of claim 1, wherein the source of electromagnetic radiation is a non-ablative laser.

7. The method of claim 1, further comprising applying an immune response modifier to the target zone.

8. The method of claim 1, wherein Hemagglutination inhibition (HAI) antibody titer in the mammalian subject is increased following vaccination compared to HAI antibody titer in a mammalian subject intradermally injected with the vaccine but not receiving the dose of electromagnetic radiation to produce the at least one thermally denatured zone.

9. The method of claim 1, wherein IgG antibody titer in the mammalian subject is increased following vaccination compared to IgG antibody titer in a mammalian subject intradermally injected with the vaccine but not receiving the dose of electromagnetic radiation to produce the at least one thermally denatured zone.

10. The method of claim 1, wherein the immune response is an increase in a helper T cell immune response in the mammalian subject and the increase is relative to the helper T cell immune response in a mammalian subject intradermally injected with the vaccine but not receiving the dose of electromagnetic radiation to produce the at least one thermally denatured zone.

11. The method of claim 1, wherein the vaccine is at least one of a bacterial vaccine, a viral vaccine, a pandemic vaccine, or a pathogenic vaccine.

12. A system for enhancing the efficacy of a vaccine, the system comprising:
    a fractional arrangement configured to simultaneously generate a plurality of regions of thermal denaturation in a target zone of biological tissue; and
    a delivery arrangement including a reservoir containing a vaccine, the delivery arrangement configured to deliver a dose of the vaccine into the target zone,
    wherein an immune response in a mammalian subject is improved following a delivery of the vaccine as a result of the generation of the plurality of regions of thermal denaturation in the target zone of biological tissue, and
    wherein the fractional arrangement and the delivery arrangement are provided in a single housing.

13. The system of claim 12, wherein a width of each of the regions is less than 1 millimeter.

14. The system of claim 12, wherein the fractional arrangement comprises a source of optical energy.

15. The system of claim 12, wherein the fractional arrangement comprises:
- a plurality of needles configured to contact or penetrate into the target zone, and
- a source of radio frequency (rf) or thermal energy configured to be directed to the needles to generate the regions of thermal denaturation.

16. The system of claim 12, wherein the fractional arrangement comprises a source of ultrasound energy configured to generate the regions of thermal denaturation.

17. The system of claim 12, wherein the vaccine is at least one of a bacterial vaccine, a viral vaccine, a pandemic vaccine, or a pathogenic vaccine.

* * * * *

UNITED STATES PATENT AND TRADEMARK OFFICE
CERTIFICATE OF CORRECTION

PATENT NO. : 11,510,983 B2
APPLICATION NO. : 14/776296
DATED : November 29, 2022
INVENTOR(S) : Mei X. Wu et al.

It is certified that error appears in the above-identified patent and that said Letters Patent is hereby corrected as shown below:

In the Specification

Column 26, Line 67, "et at" should be --et al--.

Column 27, Line 13, "et at" should be --et al--.

Signed and Sealed this
Twenty-eighth Day of February, 2023

Katherine Kelly Vidal
*Director of the United States Patent and Trademark Office*